(12) United States Patent
Dandiker et al.

(10) Patent No.: US 12,213,953 B2
(45) Date of Patent: Feb. 4, 2025

(54) EXTENDED RELEASE MIDODRINE HYDROCHLORIDE COMPOSITIONS AND METHODS OF USE

(71) Applicant: XENAMED CORP., St. Paul, MN (US)

(72) Inventors: Yogesh Dandiker, Edina, MN (US); Maulik Kiritkumar Panchal, Maple Grove, MN (US); Xiao Yu, Maple Grove, MN (US)

(73) Assignee: XENAMED CORP., St. Paul, MN (US)

( * ) Notice: Subject to any disclaimer, the term of this patent is extended or adjusted under 35 U.S.C. 154(b) by 387 days.

(21) Appl. No.: 16/956,273

(22) PCT Filed: Dec. 21, 2018

(86) PCT No.: PCT/US2018/067323
§ 371 (c)(1),
(2) Date: Jun. 19, 2020

(87) PCT Pub. No.: WO2019/126770
PCT Pub. Date: Jun. 27, 2019

(65) Prior Publication Data
US 2020/0338025 A1    Oct. 29, 2020

Related U.S. Application Data

(60) Provisional application No. 62/609,842, filed on Dec. 22, 2017, provisional application No. 62/618,374, filed on Jan. 17, 2018.

(51) Int. Cl.
| | | |
|---|---|---|
| A61K 9/28 | (2006.01) | |
| A61K 9/20 | (2006.01) | |
| A61K 9/24 | (2006.01) | |
| A61K 31/137 | (2006.01) | |
| A61K 31/165 | (2006.01) | |
| A61K 31/573 | (2006.01) | |
| A61K 38/12 | (2006.01) | |

(52) U.S. Cl.
CPC .......... *A61K 31/165* (2013.01); *A61K 9/2009* (2013.01); *A61K 9/2013* (2013.01); *A61K 9/2027* (2013.01); *A61K 9/205* (2013.01); *A61K 9/2054* (2013.01); *A61K 9/2081* (2013.01); *A61K 9/209* (2013.01); *A61K 31/137* (2013.01); *A61K 31/573* (2013.01); *A61K 38/12* (2013.01)

(58) Field of Classification Search
None
See application file for complete search history.

(56) References Cited

U.S. PATENT DOCUMENTS

| | | |
|---|---|---|
| 3,131,068 A | 4/1964 | Martin et al. |
| 5,128,144 A | 7/1992 | Korsatko-Wabnegg et al. |
| 5,360,822 A | 11/1994 | Morino et al. |
| 6,761,904 B2 | 7/2004 | Bertelsen et al. |
| 7,070,803 B2 * | 7/2006 | Skinhoj ............... A61K 31/137 424/490 |
| 8,263,125 B2 | 9/2012 | Vaya et al. |
| 8,268,352 B2 | 9/2012 | Vaya et al. |
| 9,314,999 B2 | 4/2016 | Cloutier et al. |
| 9,433,592 B2 | 9/2016 | Rosa-Calatrava et al. |
| 9,457,059 B2 | 10/2016 | Tidmarsh |
| 11,202,760 B2 | 12/2021 | Dandiker et al. |
| 2002/0147232 A1 * | 10/2002 | Sundgreen ........... A61K 9/0043 514/474 |
| 2011/0076511 A1 | 3/2011 | Paolilli et al. |
| 2013/0287823 A1 | 10/2013 | Udagawa et al. |
| 2014/0154313 A1 | 6/2014 | Counts et al. |
| 2015/0328246 A1 | 11/2015 | Broman |
| 2020/0022919 A1 | 1/2020 | Dandiker et al. |
| 2020/0338025 A1 | 10/2020 | Dandiker et al. |
| 2022/0175679 A1 * | 6/2022 | Dandiker ............... A61P 9/02 |

FOREIGN PATENT DOCUMENTS

| | | |
|---|---|---|
| JP | 2003-528909 A | 9/2003 |
| WO | WO-0174334 A1 | 10/2001 |
| WO | WO 2018064490 A1 | 4/2018 |

OTHER PUBLICATIONS

International Search Report and Written Opinion for International Application No. PCT/US2018/067323, International Search Authority, United States, mailed on Mar. 5, 2019, 9 pages.
International Search Report and Written opinion for International Application No. PCT/US2017/054323, United States Patent Office, United States, mailed on Dec. 14, 2017, 8 pages.
Hou, S., and Davis, M., "Poster 303 Bladder Distension Associated with Hypotension in a Patient with Tetraplegia after Spinal Cord Injury: A Case Report," *PM&R* 8(9S):S258-S259, American Academy of Physical Medicine and Rehabilitation, United States (Sep. 2016).
Korsatko-Wabnegg, B., et al., "A study on the formulation of press-coated tablets with 'delayed-release' effect using poly-D(-)-3-hydroxybutyric acid as a coating material," *Pharmazie* 46(3):204-206, VEB Verlag Volk und Gesundheit, Germany (Mar. 1991).
Non-Final Office Action for U.S. Appl. No. 16/338,317, mailed on Dec. 3, 2020, 9 pages.
Final Office Action for U.S. Appl. No. 16/338,317, mailed on Mar. 15, 2021, 6 pages.

\* cited by examiner

*Primary Examiner* — Susan T Tran
(74) *Attorney, Agent, or Firm* — Sterne, Kessler, Goldstein & Fox P.L.L.C.

(57) ABSTRACT

This disclosure provides pharmaceutical compositions comprising midodrine, a pharmaceutically acceptable salt thereof, desglymidodrine, or a pharmaceutically acceptable salt thereof, that can be administered to a human subject in need thereof. The disclosure also provides pharmaceutical compositions for treatment of orthostatic hypotension that can be administered once or twice a day.

18 Claims, 9 Drawing Sheets

EXTENDED RELEASE MIDODRINE HYDROCHLORIDE COMPOSITIONS AND METHODS OF USE

CROSS-REFERENCE TO RELATED APPLICATIONS

This application claims priority to U.S. Provisional Patent Application No. 62/609,842, filed on Dec. 22, 2017, and U.S. Provisional Patent Application No. 62/618,374, filed Jan. 17, 2018, both of which are incorporated by reference herein in their entirety.

FIELD OF DISCLOSURE

The present disclosure relates to pharmaceutical compositions of midodrine, a pharmaceutically acceptable salt of midodrine, its active metabolite desglymidodrine, a pharmaceutically acceptable salt of desglymidodrine, or combinations thereof, methods of making the same, and methods of using the same for treating patients in need thereof.

BACKGROUND

Orthostatic hypotension (postural hypotension) causes a sudden fall in the blood pressure when a person stands up or stretches. It is caused primarily by gravity-induced blood-pooling in the lower extremities, which in turn compromises venous return, resulting in decreased cardiac output and subsequent lowering of arterial pressure.

Midodrine hydrochloride (also referred to as midodrine HCl) is a peripheral selective alpha-1-adrenergic agonist and is indicated for the treatment of orthostatic hypotension. Midodrine HCl can also be prescribed to patients with Postural Orthostatic Tachycardia Syndrome (POTS).

Midodrine hydrochloride has the chemical name (±)-2-amino-N-[2-(2,5-dimethoxyphenyl)-2-hydroxyethyl]acetamide monohydrochloride, and the structural formula shown below:

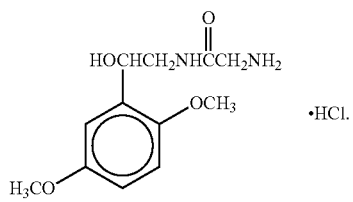

Currently, midodrine HCl is only available as an immediate release tablet. It is currently available in three strengths, 2.5 mg, 5 mg, and 10 mg. The United States FDA recommends a dosing of midodrine HCl up to 10 mg, three times a day. The tablets are to be taken at approximately 4 hour intervals, e.g., upon arising in morning, midday, and late afternoon. Midodrine HCl can cause marked elevation of supine blood pressure. In order to reduce the potential for supine hypertension during sleep, the FDA recommends that the last dose should be administered no later than 6 P.M., and in any event no later than four hours before bedtime.

Midodrine HCl is a prodrug which, upon oral administration, is rapidly absorbed and converts to its active metabolite desglymidodrine. The absolute bioavailability of midodrine (measured as desglymidodrine) is 93% for the oral tablets. The bioavailability of desglymidodrine is not affected by food. Pharmacokinetic studies have shown linear kinetics for the 2.5 mg, 5 mg, and 10 mg single doses of midodrine HCl. Moreover, it has been found that midodrine HCl has a pH independent solubility and is absorbed throughout the gastro-intestinal tract. Due to its high water solubility and high permeability, midodrine HCl is classified as a BCS Class I drug.

SUMMARY

Certain aspects of the disclosure are related to a pharmaceutical composition comprising: a first release portion comprising an active agent in a range of about 20% to about 40% (w/w) of a total amount of the active agent in the composition; and a second release portion comprising the active agent in a range of about 60% to about 80% (w/w) of the total amount of the active agent in the composition, wherein the in vitro release rate of the active agent measured by an in vitro dissolution test comprises (i) a first release that is relatively fast and (ii) a second release with no second rise in release rate taking place about 5 hours to about 10 hours after start of the in vitro dissolution test, and wherein the active agent is selected from the group consisting of midodrine, a pharmaceutically acceptable salt of midodrine, desglymidodrine, a pharmaceutically acceptable salt of desglymidodrine, and any combination thereof. In some embodiments, the second release is steady or slower than the first release. In some embodiments, the second release comprises a second rise in release rate taking place about 2 to about 4.5 hours after start of the in vitro dissolution test. In some embodiments, the second rise in release rate takes place 2 hours to 4.5 hours after start of the in vitro dissolution test. In a preferred embodiment, the in vitro dissolution test conditions are as follows: USP Apparatus I (baskets) at 100 rpm in 900 mL at 37° C., 0-2 hours, 0.1N HCl (pH 1.2); 2-4 hours, acetate buffer (pH 4.5); 4-16 hours, phosphate buffer (pH 6.8).

Other aspects of the disclosure are related to a pharmaceutical composition comprising: a first release portion comprising an active agent in a range of about 20% to about 40% (w/w) of a total amount of the active agent in the composition; and a second release portion comprising the active agent in a range of about 60% to about 80% (w/w) of the total amount of the active agent in the composition, wherein the in vitro release rate of the active agent measured by an in vitro dissolution test comprises (i) a first release that is relatively fast, (ii) a second release which includes a second rise in release rate taking place about 2 hours to about 4.5 hours after start of the in vitro dissolution test, and (iii) a third release which includes a third rise in release rate taking place about 5 hours to about 8 hours after start of the in vitro dissolution test, and wherein the active agent is selected from the group consisting of midodrine, a pharmaceutically acceptable salt of midodrine, desglymidodrine, a pharmaceutically acceptable salt of desglymidodrine, and any combination thereof. In some embodiments, the second rise in release rate takes place about 2 to about 4 hours after start of the in vitro dissolution test. In some embodiments, the second rise in release rate takes place 2 to 4.5 hours or 2 to 4 hours after start of the in vitro dissolution test. In some embodiments, the third rise in release rate takes place at least 6 hours after start of the in vitro dissolution test.

Another aspect of the disclosure is directed to a pharmaceutical composition comprising: a first release portion comprising about 1.5 mg to about 45 mg of active agent and an excipient, wherein the active agent is present in an amount of about 2% to about 40% of the total weight of the first release portion; and a second release portion comprising about 3.5 mg to about 105 mg of active agent and a rate controlling agent, wherein the active agent is present in an amount of about 2% to about 20% of the total weight of second release portion, and the amount of active agent in the second release portion to the amount of rate controlling agent is a ratio of about 1:1 to about 1:30 (w/w), wherein the active agent is selected from the group consisting of midodrine, a pharmaceutically acceptable salt of midodrine, desglymidodrine, a pharmaceutically acceptable salt of desglymidodrine, and any combination thereof.

In some embodiments, the pharmaceutical composition comprises a total amount of about 5 mg to about 150 mg of an active agent selected from the group consisting of midodrine, a pharmaceutically acceptable salt of midodrine, desglymidodrine, a pharmaceutically acceptable salt of desglymidodrine, or any combination thereof. In some embodiments, the active agent is midodrine or a pharmaceutically acceptable salt of midodrine. In some embodiments, the active agent, e.g., midodrine or a pharmaceutically acceptable salt thereof, is present in a total amount of about 7.5 mg to about 120 mg. In some embodiments, the active agent is present in a total amount of about 15 mg to about 75 mg (e.g., about 20 mg). In some embodiments, the total amount of active agent in the pharmaceutical composition is at least 15 mg (e.g., about 15 mg to 50 mg, about 18 mg to about 45 mg, or about 20 mg to about 30 mg). In some embodiments, the pharmaceutical composition is a tablet, a capsule, or a suspension.

In some embodiments, the active agent, e.g., midodrine or a pharmaceutically acceptable salt thereof, is present in the first release portion in an amount of about 1.5 mg to about 45 mg (e.g., about 4.5 mg to about 18 mg, or about 5 mg), and in the second release portion in an amount of about 3.5 mg to about 105 mg (e.g., about 10.5 mg to about 42 mg, or about 15 mg). In some embodiments, the first release portion is in the form of a layer of a multilayer tablet or a multiparticulate (e.g., pellets, particles, granules, beads, spheres, or mini-tablets) of a capsule or suspension. In some embodiments, the second release portion is in the form of one or more layers of a multilayer tablet or one or more multiparticulates of a capsule or suspension.

In some embodiments, the in vitro release rate of active agent, measured by an in vitro dissolution test, has (i) a first release that is relatively fast and (ii) a second release that is steady or slower than the first release with no second rise taking place about 5 hours to about 10 hours after start of the in vitro dissolution test. In some embodiments, there is no second rise in release rate that takes place 5 hours to 10 hours after start of the in vitro dissolution test.

In some embodiments, the in vitro release rate of active agent, measured by an in vitro dissolution test, has (i) a first release that is relatively fast and (ii) a second release comprising a second rise in release rate that takes place about 2 hours to about 4.5 hours after start of the in vitro dissolution test with no second rise taking place about 5 hours to about 10 hours after start of the in vitro dissolution test. In some embodiments, there is a second rise in release rate that takes place 2 hours to 4.5 hours after start of the in vitro dissolution test, and there is no second rise in release rate that takes place 5 hours to 10 hours after start of the in vitro dissolution test.

In some embodiments, the in vitro release rate of active agent, measured by an in vitro dissolution test, has (i) a first release that is relatively fast, (ii) a second release which includes a second rise in release rate that takes place about 2 hours to about 4.5 hours after start of the in vitro dissolution test, and (iii) a third release which includes a third rise in release rate that takes place about 5 hours to about 8 hours after start of the in vitro dissolution test. In some embodiments, there is a second rise in release rate that takes place 2 hours to 4.5 hours after start of the in vitro dissolution test, and there is a third rise in release rate that takes place 5 hours to 8 hours after start of the in vitro dissolution test.

In some embodiments, substantially all of the active agent in the first release portion is released within about 45 minutes after start of the in vitro dissolution test. In some embodiments, substantially all of the active agent in the first release portion is released within about 30 minutes after start of the in vitro dissolution test. In some embodiments, substantially all of the active agent in the second release portion is released within 16 hours, 15 hours, 14 hours, 13 hours, 12 hours, 11 hours, 10 hours, 9 hours, or 8 hours after start of the in vitro dissolution test. In some embodiments, the in vitro dissolution test is performed with USP Apparatus I (baskets) at 100 rpm in 900 mL at 37° C., 0-2 hours, 0.1N HCl (pH 1.2); 2-4 hours, acetate buffer (pH 4.5); 4-16 hours (or 4-12 hours), phosphate buffer (pH 6.8).

In some embodiments, at least about 20% of the total amount of active agent in the composition is released within about 1 hour and at least about 80% of the total amount of active agent in the composition is released within about 12 hours after the start of an in vitro dissolution test. In some embodiments, the first release is characterized by release of about 20% to about 40%, about 20% to about 35%, about 20% to about 30%, about 25% to about 40%, about 25% to about 35%, or about 30% to about 40% (e.g., 20-40%, 20-35%, 20-30%, 25-40%, 25-35%, or 30-40%) (w/w) of the total amount of the active agent in the pharmaceutical composition within about 1 hour after start of the in vitro dissolution test, and the second release is characterized by a release rate of the remaining total amount of the active agent in the pharmaceutical composition which is slower than the release rate of the first phase, wherein at least about 95% of the total amount of active agent in the pharmaceutical composition is released within about 16 hours, 15 hours, 14 hours, 13 hours, 12 hours, 11 hours, 10 hours, 9 hours, or 8 hours after the start of the in vitro dissolution test.

In some embodiments, about 20% to about 40% (w/w) of the total amount of the active agent in the pharmaceutical composition is released within about 1 hour after the start of the in vitro dissolution test. In some embodiments, at least about 95% (w/w) of the total amount of the active agent in the pharmaceutical composition is released within about 16 hours, about 15 hours, about 14 hours, about 13 hours, about 12 hours, about 11 hours, about 10 hours, about 9 hours or about 8 hours after the start of the in vitro dissolution test.

In some embodiments, the in vitro release rate of active agent during the second release phase is slower compared to the in vitro release rate of active agent released during the first phase. In some embodiments, there is no second rise in the in vitro dissolution release rate taking place 5 hours to 10 hours after start of the in vitro dissolution test. In some embodiments, there is a second rise in the in vitro dissolution release rate taking place 2 hours to 4.5 hours after start of the in vitro dissolution test.

In some embodiments, substantially all of the active agent in the first release portion is released within about 1 hour after administration of the pharmaceutical composition to a subject; and substantially all of the active agent in the second release portion is released over a period of time starting at about 1 hour after administration of the composition to the subject and up to about 16 hours, 15 hours, 14 hours, 13 hours, 12 hours, 11 hours, 10 hours, 9 hours, or 8 hours after administration of the composition to a subject.

In some embodiments, administration of about 15 mg extended release composition to a subject provides (i) a relatively fast peak plasma concentration reaching at least about 12 ng/ml (e.g., at least 12 ng/ml, at least 13 ng/ml, or at least 14 ng/ml) of desglymidodrine and (ii) at least about 7 ng/ml (e.g., at least 7 ng/ml, at least 8 ng/ml, at least 9 ng/ml, or at least 10 ng/ml) plasma concentration of desglymidodrine for at least 8 hours or at least 10 hours. It is expected that administration of about 7.5 mg extended release composition to a subject provides about half the peak plasma concentration indicated above, i.e., at least about 6 ng/ml (e.g., at least 6 ng/ml, at least 6.5 ng/ml, or at least 7 ng/ml). Similarly it is expected that administration of about 30 mg extended release composition to a subject provides about double the peak plasma concentration indicated above, i.e., at least about 24 ng/ml (e.g., at least 24 ng/ml, at least 26 ng/ml, or at least 28 ng/ml).

In some embodiments, the pharmaceutical composition is in the form of a tablet, capsule, orally disintegrating tablet, chewable tablet, buccal adhesive tablet, sublingual tablet, oral suspension, powder for oral suspension, or multi-particulates for oral suspension. In some embodiments, the pharmaceutical composition is in the form of a multilayer tablet (e.g., a bi-layer tablet or tri-layer tablet). In some embodiments, the pharmaceutical composition is in the form of a capsule. In some embodiments, the pharmaceutical composition is in the form of a suspension, for example, multi-particulates (e.g., pellets, particles, granules, beads, spheres, or mini-tablets) in a liquid vehicle.

In some embodiments, the pharmaceutical composition comprises a rate controlling agent. In some embodiments, the rate controlling agent is present in a weight ratio of the active agent in the second release portion of the composition to the rate controlling agent of about 1:1 to about 1:30 (w/w), optionally 1:2 to 1:20 (w/w), 1:3 to 1:15 (w/w), 1:5 to 1:20 (w/w), or 1:5 to 1:15 (w/w). In some embodiments, the rate controlling agent is selected from the group consisting of a water soluble excipient, a water-insoluble excipient, a water permeable excipient, and a combination thereof. In some embodiments, the pharmaceutical composition further comprises one or more of the following: a binder, a diluent, a disintegrant, a surfactant, a pigment, a lubricant, a glidant, a flavoring agent, a pH adjusting agent, a solubilizing agent, a wetting agent, a buffering agent, or any combination thereof.

In some embodiments, the first release portion herein comprises a fast release portion, e.g., an immediate release or an extended release portion. In some embodiments, the second release portion herein comprises an extended release.

In some embodiments, the pharmaceutical composition is a multilayer tablet, e.g., a bi-layer tablet comprising a first release portion comprising a fast release (e.g., an immediate release) layer and a second release portion comprising an extended release layer, or a tri-layer tablet comprising a first release portion comprising a fast release (e.g., an immediate release) layer and a second release portion comprising two extended release layers. In some embodiments, the pharmaceutical composition is a capsule or suspension comprising a first release portion comprising fast release multi-particulates (e.g., immediate release pellets) and a second release portion comprising extended release multi-particulates (e.g., extended release pellets).

In some embodiments, the portions are layers of a multilayer tablet, e.g., a bi-layer tablet or a tri-layer tablet. In another embodiment, the pharmaceutical composition is a multilayer tablet for oral administration to a subject comprising a first release layer (e.g., an immediate release layer) and a second release layer (e.g., an extended release layer). In some embodiments, the multilayer tablet is a bi-layer tablet. In some embodiments, the multilayer tablet is a tri-layer tablet comprising two extended release layers. In some embodiments, the first release layer (e.g., immediate release layer) and one or more second release layers (e.g., extended release layers) each include an active agent selected from the group consisting of midodrine, a pharmaceutically acceptable salt of midodrine, desglymidodrine, a pharmaceutically acceptable salt of desglymidodrine, and a combination thereof. In some embodiments, the first release layer includes an amount of the active agent in the range of about 1.5 mg to 45 mg and the second release layer or layers include an amount of the active agent in the range of about 3.5 mg to about 105 mg. In some embodiments, the first release layer is formulated to release about 20% to about 40% (e.g., about 30%) w/w of the total amount of active agent in the tablet within about one hour in an in vitro dissolution test; and the second release layer or layers are formulated to release about 60% to about 80% (e.g., about 70%) w/w of the total amount of active agent in the tablet over a prolonged duration starting at about 1 hour and extending to at least about 8 hours, about 10 hours, about 12 hours, about 14 hours, or about 16 hours. In some embodiments, the active agent in the second release layer or layers is released starting at about 1 hour after administration of the multilayer tablet to the subject and at least about 95% of the active agent in the second release layer or layers is released by about 16 hours, 15 hours, 14 hours, 13 hours, 12 hours, 11 hours, 10 hours, 9 hours, or 8 hours after the administration of the multilayer tablet to the subject.

In some embodiments, the second release (e.g., extended release) layer or layers of a multilayer tablet or the second release (e.g., extended release) multi-particulates of a capsule or suspension further comprise a rate controlling agent. In some embodiments, the rate controlling agent is selected from the group consisting of water-soluble, water-insoluble, water permeable, or water-impermeable excipients, and mixtures thereof. In some embodiments, the extended release layer or layers comprise a ratio of at least 1:1 to 1:30 (e.g., 1:2 to 1:20 (w/w), 1:5 to 1:20 (w/w), or 1:5 to 1:15 (w/w)) of the amount of the active agent in the second release layer to the amount of a rate controlling agent in the second release layer. The multilayer tablet, capsule, or suspension can also include one or more fillers, pigments, lubricants, glidants, binders, diluents, disintegrants, surfactants, flavoring agents, pH adjusting agents, solubilizing agents, wetting agents, buffering agents, or combinations thereof.

In some embodiments, the pharmaceutical composition comprises a first release portion and a second release portion. In some embodiments, the first release portion comprises about 4 mg of midodrine hydrochloride, and the second release portion comprises about 16 mg of midodrine hydrochloride. In some embodiments, the second release portion further comprises a rate controlling agent comprising a hydrophilic polymer and a non-polymeric agent. In some embodiments, the rate controlling agent comprises a methacrylic acid copolymer and a fatty acid ester. In some embodiments, the rate controlling agent comprises methacrylic acid and ethyl acrylate copolymer (1:1) and glyceryl behenate.

Further aspects of the disclosure are directed to a method for treating or reducing the incidence of orthostatic hypotension or postural orthostatic tachycardia syndrome (POTS) in a subject comprising administering a pharmaceutical composition, e.g., a multi-layer tablet, a capsule, or a suspension of the disclosure. In some embodiments, the pharmaceutical composition is administered once or twice a day.

In some embodiments, the total single daily dose of the pharmaceutical composition administered to the subject is greater (e.g., 10-40%, 10-35%, 10-30%, 15-40%, 15-35%, 15-30%, or about 25% greater) than the total daily dose of an immediate release tablet (e.g., 5 mg tablet) given three times daily. For example, a 20 mg dose of a pharmaceutical composition disclosed herein can be administered once daily (total daily dose 20 mg) in place of one 5 mg immediate release tablet given three times daily (total daily dose 15 mg). In some embodiments, a 10 mg dose of a pharmaceutical composition disclosed herein can be administered once daily (total daily dose 10 mg) in place of one 2.5 mg immediate release tablet given three times daily (total daily dose 7.5 mg). In some embodiments, a 40 mg dose of a pharmaceutical composition disclosed herein can be administered once daily (total daily dose 40 mg) in place of one 10 mg immediate release tablet given three times daily (total daily dose 30 mg). In some embodiments, the 10 mg, 20 mg, or 40 mg dose is a multi-layer tablet (e.g., a bi-layer or tri-layer tablet) comprising a fast release portion and an extended release portion.

In some embodiments, the subject suffers from orthostatic hypotension, dysautonomia, postural orthostatic tachycardia syndrome (POTS), retrograde ejaculation or other disorder of semen ejaculation, Bradbury-Eggleston, Shy-Drager syndromes, diabetes mellitus disease, or Parkinson's disease. In some embodiments, the subject suffers from orthostatic hypotension due to autonomic failure.

In another embodiment, a kit is provided. In some embodiments, the kit comprise multi-particulates (e.g., pellets, particles, granules, beads, spheres, or mini-tablets) disclosed herein and a liquid vehicle, wherein the multi-particulates can be combined with a liquid vehicle to form a suspension. In some embodiments, the kit includes a first formulation and a second formulation, wherein the first and second formulations being the same or different, and the first formulation being a composition comprising a first release portion and a second release portion, wherein both the first release portion and the second release portion include an active agent selected from the group consisting of midodrine, a pharmaceutically acceptable salt of midodrine, desglymidodrine, a pharmaceutically acceptable salt of desglymidodrine, and a combination thereof; the active agent is present in the first release portion in the range of about 1.5 mg to 45 mg, the active agent is present in the second release portion in the range of about 3.5 mg to about 105 mg; the first release portion is formulated to release about 20% to about 40%, about 20% to about 35%, about 20% to about 30%, about 25% to about 40%, about 25% to about 35%, about 30% to about 40%, or about 30% to 35% w/w of the total amount of active agent in the tablet within about one hour; and the second release portion is formulated to release the remaining of the total amount of active agent in the tablet (e.g., about 60-80%, e.g., about 70%) over a time period starting at about 1 hour to about 16 hours after the start of the in vitro dissolution test.

In some embodiments, the second formulation of the kit can be an immediate release formulation containing an active agent selected from the group consisting of midodrine, a pharmaceutically acceptable salt of midodrine, desglymidodrine, a pharmaceutically acceptable salt of desglymidodrine, and a combination thereof, wherein the active agent is present in the range of 2.5 mg to 20 mg and is formulated to release substantially all of the active agent within about 1 hour of administration of the second formulation to a subject.

DETAILED DESCRIPTION

Figure 1:
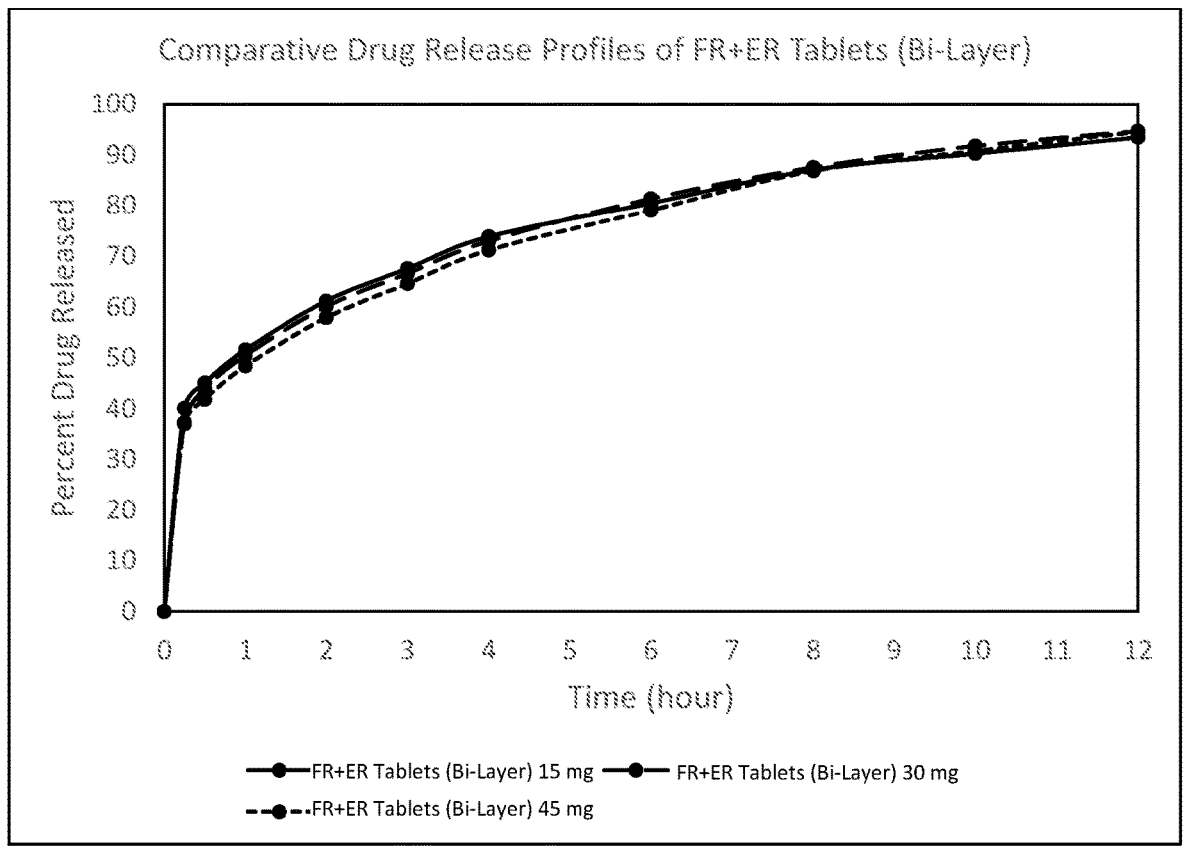
FIG. 1 is a graph that compares the in vitro dissolution profiles (shown as percentage of active agent released over a period of 12 hours) for fast release/extended release bi-layer tablet formulations of 15 mg, 30 mg, and 45 mg of midodrine HCl.

Certain aspects of the disclosure are directed to a pharmaceutical composition comprising an active agent, e.g., midodrine, a pharmaceutically acceptable salt of midodrine, desglymidodrine, a pharmaceutically acceptable salt of desglymidodrine, or any combination thereof (e.g., midodrine HCl or desglymidodrine), that first releases a portion of the active agent relatively fast, e.g., at least within the first 1 hour after administration, to a subject and releases the second (or remaining) portion of the active agent over an extended period of time, e.g., a period of up to about 8 hours, about 10 hours, about 12 hours, about 14 hours, or about 16 hours, after administration to the subject. The disclosed unique fast release/extended release (FR+ER) formulations can (i) provide a plasma level of at least 12 ng/mL (e.g., at least 14 ng/mL) of desglymidodrine within 1 hour and (ii) maintain a plasma level of at least 3 ng/mL, at least 7 ng/mL, at least 10 ng/mL, at least 12 ng/mL, or at least 14 ng/mL of desglymidodrine for a period of time, e.g., about 4 to about 12 hours (e.g., at least 8 hours) after administration of a single dose, and can maintain blood pressure of a subject in need thereof (e.g., a orthostatic hypotension patient) within desired levels (e.g., greater than 90 mmHg systolic and greater than 60 mmHg diastolic, e.g., about 120/80 mmHg) throughout the day (e.g., at least 8 hours, at least 10 hours, at least 12 hours, at least 14 hours, or at least 16 hours).

In some embodiments, the present disclosure provides improved formulations of midodrine, a pharmaceutically acceptable salt of midodrine, desglymidodrine, a pharmaceutically acceptable salt of desglymidodrine, or any combination thereof (e.g., midodrine HCl or desglymidodrine) that delivers a higher dose initially followed by controlled release that maintains blood pressure in a desired range throughout the day.

Upon oral administration of a 10 mg immediate release tablet, the plasma levels of midodrine peak after about 30 minutes, and then decline, with a half-life of approximately 25 minutes, while the active metabolite, desglymidodrine, reaches a first peak blood concentration (e.g., about 10 ng/mL) about 1 to 2 hours after the initial administration of midodrine and has a half-life of about 3 to 4 hours. The short half-lives of midodrine and desglymidodrine associated with an immediate release tablet require frequent dosing to maintain a minimum effective blood concentration (e.g., minimum of 3 ng/mL or 7 ng/mL) of desglymidodrine throughout the day.

Patients suffering from orthostatic hypotension report feeling worse in the morning, compared to afternoon and evening, even after taking a first dose of currently available 2.5 mg, 5 mg, and 10 mg immediate release tablets (TID). For example, a simulated plasma profile of desglymidodrine (the active metabolite of midodrine HCl) for 5 mg immediate release tablets administered three times a day at intervals of 4 hours, shows that the first dose would not produce as high a level of desglymidodrine as the third dose (see FIG. 3). This modeling assay suggests that desglymidodrine level increases with respective doses and reaches a maximum concentration after administration of the third dose. However, this simulated data suggest that the plasma concentration is not reaching levels of at least about 12 ng/mL or about 14 ng/mL of desglymidodrine for patients who are on, e.g., 5 mg immediate release TID regimen after the first IR dose. In some embodiments, the first release/second release formulations disclosed herein provide a plasma concentration of at least about 12 ng/mL or at least about 14 ng/mL of desglymidodrine within an hour of administration. In some embodiments, the first release/second release formulations disclosed herein maintain a plasma concentration of at least about 7 ng/mL or at least about 10 ng/mL of desglymidodrine for at least 8 hours, at least 10 hours, or at least 12 hours after administration. Thus, the first release/second release formulations disclosed herein provide improved properties over the currently marked IR (TID) formulations.

Besides a short half-life resulting in frequent dosing (e.g., 3× daily), another issue with the immediate release formulations is that the administration of multiple doses does not sufficiently maintain a patient's blood pressure for extended periods of time to manage a patient's symptoms such as dizziness and/or light headedness throughout the day. For example, multiple doses of immediate release midodrine can result in repeated rises and falls in the patient's blood pressure as the active agent is released upon each administration and subsequently eliminated. In some embodiments, the first release/second release formulations disclosed herein reduce a patient's symptoms such as dizziness and/or light headedness throughout the day.

Additionally, the multiple dosing (e.g., 3× daily) of immediate release tablets decreases patient compliance. Missing or delayed administration of an immediate release dose can result in the patient's condition becoming worse and sometimes unmanageable. The present application provides a formulation of the drug that can be given less frequently, e.g., 1x daily, than the immediate release tablets and thereby improving patient compliance.

Definitions

As used herein, the following words and phrases are generally intended to have the meanings as set forth below, except to the extent that the context in which they are used indicates otherwise.

It is noted that as used in the specification and the appended claims, the singular forms "a," "an," and "the" include plural reference unless the context clearly dictates otherwise.

The term "about" as used herein means approximately 10%. When the term "about" is used in conjunction with a numerical value or range, it modifies that value or range by extending the boundaries above and below the numerical values set forth. In general, the term "about" is used herein to modify a numerical value above and below the stated value by a variance of 10 percent, up or down (higher or lower), i.e., ±10%, unless a different variance is indicated (e.g., ±30%, ±20%, ±5%, ±1%, etc.).

Also as used herein, "and/or" refers to and encompasses any and all possible combinations of one or more of the associated listed items, as well as the lack of combinations when interpreted in the alternative ("or").

The term "active agent" refers to a substance, including a biologically active substance, that is useful for prophylactic and/or therapeutic treatment. Typically, the active agents are organic molecules that are drug compounds, their salts, metabolites, etc. The term "active agent" as used in this disclosure can refer to midodrine, a pharmaceutically acceptable salt of midodrine, its active metabolite desglymidodrine, a pharmaceutically acceptable salt of desglymidodrine, or a combination thereof. For example, the active agent can be midodrine HCl.

The term "midodrine" refers to the compound having the following chemical structure:

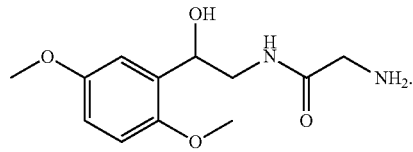 [SMILES: COc1ccc(OC)c(C(O)CNC(=O)CN)c1]

For purposes of this disclosure, unless indicated otherwise, when referring to a formulation or pharmaceutical composition comprising "midodrine", it should be understood that the embodiment can include midodrine or a pharmaceutically acceptable salt of midodrine, e.g., midodrine HCl.

The term "desglymidodrine" refers to the active metabolite of midodrine having the following chemical structure:

For purposes of this disclosure, unless indicated otherwise, when referring to a formulation or pharmaceutical composition comprising "desglymidodrine", it should be understood that the embodiment can include desglymidodrine or a pharmaceutically acceptable salt of desglymidodrine.

The term "pharmaceutically acceptable salt" of a given compound refers to salts that retain the biological effectiveness and properties of the given compound, and which are not biologically or otherwise undesirable. "Pharmaceutically acceptable salts" include, for example, salts with inorganic acids and salts with an organic acid. Compounds described herein as an acid addition salt may be formed into a corresponding the free base by basifying a solution of the acid salt. Conversely, an addition salt, particularly a pharmaceutically acceptable addition salt, may be produced by dissolving a corresponding free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example, sodium, potassium, lithium, ammonium, calcium and magnesium salts. Salts derived from organic bases include, but are not limited to, salts of primary, secondary and tertiary amines. In one embodiment, a pharmaceutically acceptable salt of midodrine or desglymidodrine is a hydrochloride salt.

The term "portion" as used herein refers to a part, a percentage, or a share of a whole or total (e.g., a whole tablet or a total amount of active agent).

The term "substantially all" as used herein refers to most of the total amount, e.g., at least 80%, at least 85%, at least 90%, at least 95% of a total amount.

The term "subject," as used herein, refers to a human, e.g., a human patient.

The term "first release portion" or "fast release portion" as used herein refers to a part of the pharmaceutical composition disclosed herein that releases the active agent contained therein relatively fast, e.g., within about 1 hour after the start of an in vitro dissolution test. In some embodiments, the first release portion comprises an immediate release delivery system.

In some embodiments, the in vitro dissolution conditions for the fast release/extended release compositions disclosed herein are designed to mimic the in vivo release conditions. In a preferred embodiment, the in vitro dissolution test conditions are as follows: USP Apparatus I (baskets) at 100 rpm in 900 mL at 37° C., 0-2 hours, 0.1N HCl (pH 1.2); 2-4 hours, acetate buffer (pH 4.5); 4-16 hours, phosphate buffer (pH 6.8).

The term "immediate release" as used herein refers to a delivery system by which at least a portion of the active agent is released from a pharmaceutical composition or formulation without delay. In some embodiments, the immediate release of the active agent is within about 30 minutes to about 1 hour after the start of an in vitro dissolution test. In some embodiment, the immediate release of the active agent is within about 1 hour after administration to a subject.

The term "second release portion" or "extended release portion" as used herein refers to a part of the pharmaceutical composition disclosed herein that releases the active agent contained therein over a time period. In some embodiments, the second release portion comprises an extended release delivery system.

The term "extended release" as used herein refers to a delivery system by which the active agent is released over a time period (i.e., an extended release period). In some embodiments, the pharmaceutical composition can extend the release of at least a portion of the active agent over a period up to about 8 hours, up to about 10 hours, up to about 12 hours, up to about 14 hours, about 16 hours, from about 1 hour to about 16 hours, from about 1 hour to 14 hours, from about 1 hour to about 12 hours, from about 1 hour to about 10 hours, from about 1 hour to about 8 hours after the start of an in vitro dissolution test. In some embodiment, the extended release of the active agent is over a period up to about 8 hours, up to about 10 hours, up to about 12 hours, up to about 14 hours, about 16 hours, from about 1 hour to about 16 hours, from about 1 hour to 14 hours, from about 1 hour to about 12 hours, from about 1 hour to about 10 hours, from about 1 hour to about 8 hours after administration to a subject.

The term "rate controlling agent" refers to an agent whose primary function is to modify the duration of release of the active drug substance from a dosage form.

"Percent" or "%" as used herein refers to weight (w/w) percentage unless otherwise specified.

The term "percent drug released" as used herein refers to the percentage (w/w) of the active agent released from a pharmaceutical composition at a specified time as compared to the total amount of the active agent in the pharmaceutical composition. For example, if a pharmaceutical composition releases 20 wt % of the total active at 1 hour, 28 wt % at 2 hour, and 35 wt % at 3 hour in a dissolution test, then the percent drug released of this pharmaceutical composition is 20% (w/w) at 1 hour, 28% (w/w) at 2 hour, and 35% (w/w) at 3 hour.

The term "release rate" refers to the amount of active agent released from the pharmaceutical composition over a period of time. For example, the release rate can be reported as the amount of active agent released per hour (e.g., mg/hr) or the percentage of the active agent released per hour (e.g., %/hr). The release rate can be measure with an in vitro test, such as an in vitro dissolution test, or an in vivo test. As described herein, the drug release rate can be measured approximately by incremental increases in the percent drug released at a specified time point as compared to the preceding time point in an in vitro dissolution test. For example, if the percent drug released of a pharmaceutical composition is 20% (w/w) at 1 hour, 28% (w/w) at 2 hour, and 35% (w/w) at 3 hour, the drug release rate can be described as 20%/hr at 1 hour, 8%/hr at 2 hour, and 7%/hr at 3 hour.

The term "release profile" refers to an in vitro dissolution curve representing the amount or percentage of active agent measured at specific time points. Or, the term "release profile" can also refer to an in vivo plasma curve representing the active agent plasma concentration measured at specific time points.

The term "rise" as used herein refers to an increase of the active agent release rate from a composition to a peak (or shoulder or plateau) in its in vitro dissolution release profile and/or the term "rise" can also refer to an increase of the active agent plasma concentration to a peak (or shoulder or plateau) in its in vivo release profile. As discussed above, the active agent release rate in an in vitro dissolution test can be approximately described by the incremental increase in the percent active agent released at a specified time point as compared to the preceding time point in the dissolution test.

The term "second rise" as used herein refers to an increase of the active agent release rate from a composition after the initial release or first rise. In some embodiments, the disclosed formulations do not have a second rise taking place 5 hours (e.g., between about 5-10 hours) after start of an in vitro dissolution test.

The term "third rise" as used herein refers to an increase of the active agent release rate from a composition after the initial release (or first rise) and after the second rise.

The term "treatment" or "treating" means any treatment of a disease in a mammal, including:
(i) preventing or reducing the incidence of the disease by causing the clinical symptoms of the disease not to develop;
(ii) inhibiting the disease by arresting the development of clinical symptoms of the disease; and/or
(iii) relieving the disease by causing the regression of clinical symptoms of the disease.

An "effective amount" is the quantity of compound or formulation in which a beneficial clinical outcome can be achieved when the compound or formulation is administered to a subject suffering from or at risk of suffering from a condition to be treated. A "beneficial clinical outcome" can include one or more of: a reduction in number or severity of symptoms in a subject, such as an increase in blood pressure, lack of dizziness and/or lack of light headedness.

As used herein, "multi-particulates" (used interchangeably with "a multi-particulate") refers to discrete, small drug units, exhibiting a desired characteristic, that make up a multiple unit drug delivery system. The multi-particulates can be in the form of, for example, a drug particle, a granule, a pellet, a bead, a sphere, or a mini-tablet.

Wherever aspects or features are described herein with the language "comprising," otherwise analogous aspects or features described in terms of "consisting of" and/or "consisting essentially of" are also provided. To the extent that the term "includes" or "including" is used in the specification or the claims, it is intended to be inclusive in a manner similar to the term "comprising" as that term is interpreted when employed as a transitional word in a claim.

As used herein, the terms "optional" and "optionally" mean that the subsequently described circumstance may or may not occur, so that the description includes instances where the circumstance occurs and instances where it does not.

Furthermore, to the extent that the term "or" is employed (e.g., A or B) it is intended to mean "A or B or both." When the applicants intend to indicate "only A or B but not both" then the term "only A or B but not both" will be employed. Thus, use of the term "or" herein is the inclusive, and not the exclusive use. See Bryan A. Garner, A Dictionary of Modern Legal Usage 624 (2d. Ed. 1995). Also, to the extent that the terms "in" or "into" are used in the specification or the claims, it is intended to additionally mean "on" or "onto."

In addition, where features or aspects of the disclosure are described in terms of Markush groups, those skilled in the art will recognize that the disclosure is also thereby described in terms of any individual member or subgroup of members of the Markush group. As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, and the like. As a non-limiting example, each range discussed herein can be readily broken down into a lower third, middle third and upper third, and the like. As will also be understood by one skilled in the art all language such as "up to," "at least," "greater than," "less than," include the number recited and refer to ranges which can be subsequently broken down into sub-ranges as discussed above. Finally, as will be understood by one skilled in the art, a range includes each individual member. For example, a group having 1-3 members refers to groups having 1, 2, or 3 members. Similarly, a group having 1-5 members refers to groups having 1, 2, 3, 4, or 5 members, and so forth. While various aspects and embodiments have been disclosed herein, other aspects and embodiments will be apparent to those skilled in the art.

Pharmaceutical Compositions

In some embodiments, the pharmaceutical compositions disclosed herein can contain one or more active agents. The active agents can be selected from the group consisting of midodrine, a pharmaceutically acceptable salt of midodrine, desglymidodrine, a pharmaceutically acceptable salt of desglymidodrine, and combinations thereof. In one embodiment, the active agent is midodrine or a pharmaceutically acceptable salt thereof, e.g., midodrine hydrochloride (HCl). In another embodiment, the active agent is desglymidodrine or a pharmaceutically acceptable salt thereof.

In some embodiments, the pharmaceutical compositions disclosed herein can be, but are not limited to, a tablet, a capsule, an orally disintegrating tablet, a chewable tablet, a buccal adhesive tablet, a sublingual tablet, an oral suspension, or a powder, granules, or multi-particulates for oral suspension.

In some embodiments, the pharmaceutical compositions envisioned herein with unique release profiles can include, but are not limited to:
1. a bi-layer tablet containing fast release and extended release layers;
2. a tri-layer tablet containing fast release and two extended release layers;
3. a fast release drug coating on an extended release core tablet;
4. a tablet-in-tablet dosage form that includes an extended release tablet in a fast release tablet;
5. a compression coated tablet having an extended release core and fast release coating;
6. a fast release core coated with extended release coating followed by a further fast release drug coating;
7. a capsule filled with multi-particulates (e.g., pellets, particles, granules, beads, spheres, or mini-tablets) or a tablet compressed from multi-particulates in which the multi-particulates have an extended release core and fast release coating;
8. a blend of fast release and extended release multi-particulates that may be filled within a capsule or compressed into a tablet;
9. a blend of fast release and extended release multi-particulates that may be suspended in an appropriate delivery vehicle known in the art or filled in to a sachet for reconstitution; and
10. an extended release osmotic controlled tablet with fast release drug layer coat.

In some embodiments, the fast release and extended release portions each comprise midodrine hydrochloride. In some embodiments, the fast release portion of a pharmaceutical composition comprises about 20% to about 45%, about 20% to about 40%, about 25% to about 40%, about 30% to about 40%, about 30% to about 50%, or about 30% to about 35% (e.g., 20-45%, 20-40%, 25-40%, 30-50%, 30-40%, or 30-35%) of the midodrine hydrochloride in the composition (w/w). The pharmaceutical compositions disclosed herein can be formulated for oral administration, e.g., in the form of a tablet, a suspension, or multi-particulate filled capsule.

In some embodiments, the pharmaceutical compositions disclosed herein can comprise multiple distinct and distinguishable portions which can comprise the same or different excipients. One embodiment, the pharmaceutical compositions can comprise a fast release portion and an extended release portion (e.g., wherein the fast release and extended release portions each comprise midodrine hydrochloride). In some embodiments, the pharmaceutical compositions disclosed herein can be multi-layer compositions, e.g., a multi-layer tablet, comprising more than one drug-containing layer. In certain embodiments, the pharmaceutical composition is a bi-layer tablet or a tri-layer tablet. In certain embodiments, the pharmaceutical composition is a capsule filled with fast release and extended release multi-particulates.

In some embodiments, the pharmaceutical composition disclosed herein comprises about 5 mg to about 150 mg, about 7.5 mg to about 150 mg, about 7.5 mg to about 120 mg, about 5 mg to about 100 mg, about 7.5 mg to about 100 mg, about 7.5 mg to about 75 mg, about 7.5 mg to about 50 mg, about 10 mg to about 100 mg, about 15 mg to about 100 mg, about 20 mg to about 100 mg, about 10 mg to about 75 mg, about 10 mg to about 50 mg, about 15 mg to about 75 mg, about 15 mg to about 50 mg, about 20 mg to about 75 mg, about 20 mg to about 50 mg, about 10 mg to about 20 mg, about 25 mg to about 35 mg, or about 40 mg to about 50 mg of an active agent. In one embodiment, the pharmaceutical composition can comprise about 5 mg, about 7.5 mg, about 10 mg, about 12.5 mg, about 15, mg, about 17.5 mg, about 20 mg, about 22.5 mg, about 25 mg, about 27.5 mg, about 30 mg, about 32.5 mg about 35 mg, about 37.5 mg, about 40 mg, about 42.5 mg, about 45 mg, about 47.5 mg, about 50 mg, about 60 mg, about 100 mg, about 120 mg, or about 150 mg of the active agent. In some embodiments, the active agent is midodrine hydrochloride. In some embodiments, the pharmaceutical composition disclosed herein comprises a total amount of about 20 mg of midodrine hydrochloride per dosage unit (e.g., a single tablet, capsule, or suspension dose). In some embodiments, the pharmaceutical composition disclosed herein comprises a total amount of about 10 mg of midodrine hydrochloride per dosage unit (e.g., a single tablet, capsule, or suspension dose). In some embodiments, the pharmaceutical composition disclosed herein comprises a total amount of about 40 mg of midodrine hydrochloride per dosage unit (e.g., a single tablet, capsule, or suspension dose).

In some embodiments, the pharmaceutical compositions disclosed herein comprises a fast release portion and an extended release portion. In some embodiments, the fast release portion comprises an active agent in an amount of about 15% to about 50%, about 20% to about 45%, about 20% to about 40%, about 25% to about 45%, about 25% to about 40%, about 25% to about 35%, about 30% to about 45%, about 30% to about 40%, or about 30% to about 35% of the total weight of the active agent in the composition (w/w). In another embodiment, the fast release portion can comprise an active agent in an amount of about 15%, about 20%, about 21%, about 22%, about 23%, about 24%, about 25%, about 26%, about 27%, about 28%, about 29%, about 30%, about 31%, about 32%, about 33%, about 34%, about 35%, about 40%, about 45%, or about 50% w/w of the total active agent in the composition. In some embodiments, the active agent is midodrine hydrochloride.

In another embodiment, the fast release portion can comprise an active agent in an amount that ranges from about 0.75 mg to about 75 mg, about 1 mg to about 60 mg, about 2 mg to about 50 mg, about 2.25 mg to about 36 mg, about 3 mg to about 12 mg, about 4 mg to about 20 mg, about 4.5 to about 18 mg, about 6 mg to about 24 mg, about 3 mg to about 6 mg, about 7.5 mg to about 10.5 mg, or about 12 mg to about 15 mg. In another embodiment, the fast release portion can comprise about 1 mg, about 1.5 mg, about 2 mg, about 3 mg, about 3.5 mg, about 4 mg, about 4.5 mg, about 5 mg, about 5.5 mg, about 6 mg, about 6.5 mg, about 7 mg, about 7.5 mg, about 8 mg, about 8.5 mg, about 9 mg, about 9.5 mg, about 10 mg, about 10.5 mg, about 11 mg, about 12 mg, about 12.5 mg, about 13 mg, about 13.5 mg, about 14 mg, about 14.5 mg, about 15 mg, about 15.5 mg, about 16 mg, about 16.5 mg, about 17 mg, about 18 mg, about 19 mg, about 20 mg, about 21 mg, about 22 mg, about 24 mg, about 27 mg, about 30 mg, about 36 mg, about 40 mg, about 45 mg, about 48 mg, about 54 mg, or about 67.5 mg of an active agent. In some embodiments, the active agent is midodrine hydrochloride.

In some embodiments, the extended release portion comprises an active agent in an amount of about 50% to about 85%, about 55% to about 80%, about 55% to about 75%, about 60% to about 80%, about 60% to about 75%, about 55% to about 70%, about 65% to about 70%, or about 60% to about 70% of the total weight of the active agent in the composition (w/w). In another embodiment, the extended release portion can comprise an active agent in an amount of about 50%, about 55%, about 65%, about 65%, about 70%, about 75%, about 80%, or about 85% w/w of the total active agent in the composition. In some embodiments, the active agent is midodrine hydrochloride.

In another embodiment, the extended release portion comprises an active agent in an amount that ranges from about 2.5 mg to about 127.5 mg, about 3 mg to about 110 mg, about 3.75 to about 102 mg, about 3.75 to about 102 mg, about 5.25 mg to about 84 mg, about 12 mg to about 96 mg, about 10.5 mg to about 84 mg, about 9 to about 72 mg, about 7 mg to about 14 mg, about 17.5 mg to about 24.5 mg, or about 28 mg to about 35 mg. In another embodiment, the extended release portion can comprise about 2.5, about 5 mg, about 6 mg, about 7 mg, about 7.5, about 8 mg, about 8.5 mg, about 9 mg, about 9.625 mg, about 10 mg, about 10.5 mg, about 11 mg, about 12 mg, about 12.5 mg, about 13 mg, about 13.5 mg, about 14 mg, about 15 mg, about 15.5 mg, about 16 mg, about 16.5 mg, about 17 mg, about 17.5 mg, about 18 mg, about 19 mg, about 20 mg, about 21 mg, about 22 mg, about 23 mg, about 24 mg, about 25 mg, about 26 mg, about 27 mg, about 27.5 mg, about 28 mg, about 29 mg, about 30 mg, about 31 mg, about 32 mg, about 33 mg, about 34 mg, about 35 mg, about 36 mg, about 38 mg, about 40 mg, about 42 mg, about 48 mg, about 55 mg, about 60 mg, about 66 mg, about 70 mg, about 72 mg, about 80 mg, about 84 mg, about 96 mg, about 100 mg, or about 127.5 mg of an active agent. In some embodiments, the active agent is midodrine hydrochloride.

In some embodiments, the fast release portion comprises about 3 mg to about 9 mg of midodrine hydrochloride, and the extended release portion comprises about 9 mg to about 21 mg of midodrine hydrochloride. In some embodiments, the fast release portion and the extended release portion comprise about 5 mg and about 15 mg of midodrine hydrochloride, respectively. In some embodiments, the fast release portion and the extended release portion comprise about 6 mg and about 9 mg of midodrine hydrochloride, respectively. In some embodiments, the fast release portion and the extended release portion comprise about 4 mg and about 16 mg of midodrine hydrochloride, respectively.

The extended release portion of the pharmaceutical compositions disclosed herein can comprise an effective amount of one or more rate controlling agents. The rate controlling agents can be, for example, water-soluble, water-insoluble, water permeable, water-impermeable excipients, and mixtures thereof. The rate controlling agents can be a polymer or a non-polymeric agent. The rate controlling agents can be a hydrophilic polymer or a hydrophobic polymer. In some embodiments, the rate controlling agent is incorporated into the pharmaceutical composition. In one embodiment, the rate controlling agent is incorporated into the extended release portion. In another embodiment, the extended release portion of the pharmaceutical composition is coated with the rate controlling agent.

In some embodiments, the rate controlling agent is a hydrophilic polymer selected from hypromellose; hydroxypropyl cellulose (HPC); hydroxyethyl cellulose (HEC); polyethylene oxide; polyvinyl alcohol; povidone; xanthan gum; guar gum; chitosan; a chitosan derivative; carbomer; carrageenan; carboxymethyl cellulose; sodium alginate; a polyglycolized glyceride; polyethylene glycol; a polyvinyl acetate dispersion; cellulose acetate; cellulose acetate butyrate; cellulose acetate phthalate; cellulose triacetate; methacrylic acid copolymer; hypromellose acetate succinate; and a combination thereof. In one embodiment the rate controlling agent is hypromellose. In another embodiment, the rate controlling agent is a hypromellose (e.g., USP hypromellose 2208) or METHOCEL™ K4M (COLORCON®). In some embodiments, the rate controlling agent is methacrylic acid copolymer, e.g., methacrylic acid and ethyl acrylate copolymer (1:1) (e.g., Eudragit L100-55®). In some embodiments, the rate controlling agent is hypromellose acetate succinate (e.g., AquaSolve® LG).

In other embodiments, the rate controlling agent is a hydrophobic polymer selected from poly(methyl methacrylate); poly(ethyl methacrylate); poly(methyl acrylate); poly(isopropyl acrylate); poly(isobutyl acrylate); poly(octadecyl acrylate); ethyl cellulose; cellulose propionate; cellulose acetate propionate; and a combination thereof.

In some embodiments, the rate controlling agent is a non-polymeric agent selected from a wax; a fatty alcohol; a fatty acid ester; hydrogenated vegetable oil; and a combination thereof. In some embodiments, the rate controlling agent is glyceryl behenate.

In some embodiments, the extended release portion can comprise a rate controlling agent in a weight ratio of the active agent in the extended release portion to the rate controlling agent of about 1:1 to about 1:30 (w/w), about 1:1 to about 1:20 (w/w), about 1:2 to about 1:15 (w/w), about 1:3 to about 1:15 (w/w), about 1:5 to about 1:15 (w/w), or about 1:5 to about 1:10 (w/w). In another embodiment, the extended release portion comprises a rate controlling agent in a weight ratio of the active agent in the extended release portion to the rate controlling agent of about 1:5 (w/w), about 1:7 (w/w), about 1:10 (w/w), about 1:12 (w/w), about 1:15 (w/w), about 1:20 (w/w), about 1:25 (w/w), or about 1:30 (w/w).

In some embodiments, the extended release portion can comprise a combination of two or more rate controlling agents. In some embodiments, the extended release portion can comprise a combination of two rate controlling agents. In some embodiments, the extended release portion can comprise methacrylic acid copolymer and glyceryl behenate as the rate controlling agents. In some embodiments, the extended release portion can comprise methacrylic acid and ethyl acrylate copolymer (1:1) and glyceryl behenate as the rate controlling agents.

The pharmaceutical compositions disclosed herein can comprise one or more fillers, binders, diluents, disintegrants, surfactants, pigments, lubricants, glidants, flavoring agents, pH adjusting agents, solubilizing agents, wetting agents, buffering agents, or any combinations thereof.

Examples of binders include, but are not limited to, acacia, alginic acid, carbomer, carboxymethylcellulose sodium, dextrin, ethylcellulose, gelatin, guar gum, hydrogenated vegetable oil (type I), hydroxyethyl cellulose, hydroxypropyl cellulose, hydroxypropyl methylcellulose, liquid glucose, magnesium aluminum silicate, maltodextrin, methylcellulose, microcrystalline cellulose, polymethacrylates, povidone, pregelatinized starch, sodium alginate, starch, zein, and the like, or mixtures thereof. In one embodiment, the binder is hydroxypropyl methyl cellulose, microcrystalline cellulose, or povidone.

Examples of diluents include, but are not limited to, microcrystalline cellulose, lactose, starch, sucrose, calcium phosphate anhydrous and dibasic, mannitol, sorbitol, xylitol, maltitol, ammonium alginate, calcium carbonate, calcium lactate, calcium silicate, calcium sulfate, cellulose powdered, silicified microcrystalline cellulose, compressible sugar, confectioner's sugar, corn starch, pregelatinized starch, dextrates, dextrin, dextrose, erythritol, ethyl cellulose, fructose, glyceryl palmitosterate, isomalt, lactitol monohydrate, magnesium carbonate, magnesium oxide, maltose, medium chain triglycerides, polydextrose, polymethacrylates, simethicone, sodium alginate, sodium chloride, sterilize maize and a combination thereof.

Examples of disintegrants include, but are not limited to, alginic acid, carboxymethylcellulose calcium, carboxymethylcellulose sodium, colloidal silicon dioxide, croscarmellose sodium, crospovidone, guar gum, magnesium aluminum silicate, methylcellulose, microcrystalline cellulose, polyacrilin potassium, powdered cellulose, pregelatinized starch, sodium alginate, calcium alginate, powdered cellulose, glycine, sodium starch glycolate, starch, hydroxypropyl cellulose, and the like, or mixtures thereof.

Examples of glidants include, but are not limited to, starch, talc, silicon dioxide, e.g., colloidal silicon dioxide, and the like, or mixtures thereof.

Examples of lubricants include, but are not limited to, magnesium stearate, stearic acid, talc, calcium stearate, glyceryl monostearate, glyceryl behenate, glyceryl palmitostearate, hydrogenated castor oil, hydrogenated vegetable oil, mineral oil, polyethylene glycol, sodium benzoate, sodium lauryl sulfate, magnesium lauryl sulfate, medium chain triglycerides, myristic acid, palmitic acid, poloxamer, sodium benzoate, sodium stearyl fumarate, zinc stearate, and the like, or mixtures thereof.

In some embodiments, the pharmaceutical compositions disclosed herein can be further coated with a film coating such that the film coating does not modify the release characteristics of the composition. Suitable materials that can be used to film-coat the compositions include, but are not limited to, hypromellose, hydroxy propyl cellulose, polyvinyl alcohol, ready-to-use premix like Opadry® (hypromellose, PEG) (Colorcon), Opadry® II (polyvinyl alcohol, PEG, talc, and titanium dioxide), and mixtures thereof.

The pharmaceutical compositions disclosed herein can be prepared by any number of manufacturing processes known in the art. Non-limiting examples of suitable manufacturing processes include dry granulation, wet granulation, roller compaction, extrusion/spheronization, rotary pelletization, hot melt extrusion, fluid bed granulation, fluid bed coating, compression coating, powder coating, and the like.

In some embodiments, the pharmaceutical compositions disclosed herein comprise (1) a fast release layer including: about 4 mg midodrine HCl; microcrystalline cellulose; croscarmellose sodium or sodium starch glycolate; iron oxide yellow or iron oxide red; talc; and magnesium stearate; and (2) an extended release layer including: about 16 mg midodrine HCl; methacrylic acid and ethyl acrylate copolymer (1:1) or hypromellose acetate succinate; glyceryl behenate; povidone; and magnesium stearate. In some embodiments, the fast release layer includes about 4 mg midodrine HCl, about 135 mg of microcrystalline cellulose, about 9 mg of croscarmellose sodium, about 0.75 mg of iron oxide red, about 0.75 mg of talc, and about 0.75 mg of magnesium stearate. In some embodiments, the extended release layer includes about 16 mg midodrine HCl; about 100 to 340 mg of methacrylic acid and ethyl acrylate copolymer (1:1) or hypromellose acetate succinate; about 10 to 40 mg of glyceryl behenate; about 10 to 40 mg of povidone; and about 0.6 to 1.8 mg of magnesium stearate. In some embodiments, the extended release layer includes about 16 mg midodrine HCl; about 262 mg of methacrylic acid and ethyl acrylate copolymer (1:1); about 20 mg of glyceryl behenate; about 20 mg of povidone; and about 1.5 mg of magnesium stearate.

In some embodiments, the pharmaceutical compositions disclosed herein allow for in vivo release of an active agent (e.g., midodrine hydrochloride) for up to about 16 hours, up to about 15 hours, up to about 14 hours, up to about 13 hours, up to about 12 hours, up to about 11 hours, up to about 10 hours, up to about 9 hours, or up to about 8 hours after administration to a subject, and can be characterized by a release profile in an in vitro dissolution test comprising (i) a first phase which is a fast release of the active agent and (ii) a second phase which is an extended release of the active agent. In some embodiments, the second phase release is steady or slower than the first (fast) release. In some embodiments, the second phase comprises a second rise in release rate that takes place about 2 to about 4.5 hours after start of the in vitro dissolution test. In some embodiments, the second phase does not comprise a second rise after 5 hours (e.g., no second rise takes place between 5-10 hours) from the start of the in vitro dissolution test. In some embodiments, the second phase comprises a third rise in release rate that takes place at least about 6 hours after start of the in vitro dissolution test.

In some embodiments, the first phase is characterized by the release of substantially all, at least about 80%, at least about 85%, at least about 90%, at least about 95%, at least about 96%, at least about 97%, at least about 98%, at least about 99%, or all of the active agent (e.g., midodrine hydrochloride) in the fast release portion within about 2 hours, about 90 minutes, about 1 hour, about 55 minutes, about 50 minutes, about 45 minutes, about 40 minutes, about 35 minutes, about 30 minutes, about 25 minutes, about 20 minutes, or about 15 minutes after the start of an in vitro dissolution test.

In some embodiments, the first phase is characterized by the release of about 15% to about 55%, about 20% to about 55%, about 20% to about 50%, about 20% to about 45%, about 20% to about 40%, about 25% to about 40%, about 30% to about 50%, or about 30% to about 40% (e.g., 15-55%, 20-55%, 20-50%, 20-45%, 20-40%, 25-40%, 30-50%, or 30-40%) of the total weight of the active agent (e.g., midodrine hydrochloride) in the composition within about 2 hours, about 90 minutes, about 1 hour, about 55 minutes, about 50 minutes, about 45 minutes, about 40 minutes, about 35 minutes, about 30 minutes, about 25 minutes, about 20 minutes, or about 15 minutes after the start of an in vitro dissolution test. In another embodiment, the first phase is characterized by a release of about 15% to about 55%, about 20% to about 55%, about 20% to about 50%, about 20% to about 45%, about 20% to about 40%, about 25% to about 40%, about 30% to about 50%, or about 30% to about 40% (e.g., 15-55%, 20-55%, 20-50%, 20-45%, 20-40%, 25-40%, 30-50%, or 30-40%) of the total weight of active agent in the composition in less than 1 hour, less than 55 minutes, less than 50 minutes, less than 45 minutes, less than 40 minutes, less than 35 minutes, less than 30 minutes, less than 25 minutes, less than 20 minutes, or less than 15 minutes after the start of an in vitro dissolution test.

In another embodiment, the second phase is characterized by the release of substantially all, at least about 80%, at least about 85%, at least about 90%, at least about 95%, at least about 96%, at least about 97%, at least about 98%, at least about 99%, or all of the active agent (e.g., midodrine hydrochloride) in the extended release portion over an extended or prolonged duration of about 8 to about 16 hours, about 10 to about 16 hours, about 12 to about 16 hours, about 14 to about 16 hours, about 8 to about 14 hours, about 8 to about 12 hours, about 8 to about 10 hours, about 10 to about 14 hours, about 10 to about 12 hours, or about 12 to about 14 hours (e.g., about 16 hours, about 15 hours, about 14 hours, about 13 hours, about 12 hours, about 11 hours, about 10 hours, or about 8 hours) after the start of an in vitro dissolution test. In one embodiment, the second phase is characterized by the release of substantially all, at least about 80%, at least about 85%, at least about 90%, at least about 95%, at least about 96%, at least about 97%, at least about 98%, at least about 99%, or all of the active agent in the extended release portion over a duration of between about 8 to about 12 hours, about 9 to about 12 hours, about 10 to about 12 hours, about 11 to about 12 hours, about 8 hours, about 9, hours, about 10 hours, about 11 hours, about 12 hours, about 13 hours, or about 14 hours after the start of an in vitro dissolution test.

In some embodiments, the first phase is relatively fast and the second phase is steady or slower than the first phase with no second rise about 4 hours, about 5 hours, about 6 hours, about 7 hours, about 8 hours, about 9 hours, about 10 hours, about 11 hours, about 12 hours, between about 4 to about 12 hours, between about 4 to about 11 hours, between about 4 to about 10 hours, between about 4 to about 9 hours, between about 4 to about 8 hours, between about 4.5 to about 12 hours, between about 4.5 to about 11 hours, between about 4.5 to about 10 hours, between about 4.5 to about 9 hours, between about 4.5 to about 8 hours, between about 5 to about 12 hours, between about 5 to about 11 hours, between about 5 to about 10 hours, between about 5 to about 9 hours, between about 5 to about 8 hours, between about 6 to about 12 hours, between about 6 to about 11 hours, between about 6 to about 10 hours, between about 6 to about 9 hours, or between about 6 to about 8 hours after the start of an in vitro dissolution test.

In some embodiments, the first phase is relatively fast and the second phase is steady or slower than the first phase with a second rise in release rate that takes place: about 3 hours to about 5 hours, about 3 hours to about 4.5 hours, about 3.5 to about 4.5 hours, about 4 to about 4.5 hours, about 4 hours, about 4.5 hours, prior to about 5 hours, or prior to 5 hours after the start of an in vitro dissolution test.

In some embodiments, the pharmaceutical compositions disclosed herein comprises a fast release portion and an extended release portion characterized by an in vitro dissolution release profile such that about 45% to about 75%, about 45% to about 70%, about 45% to about 65%, about 55% to about 65%, or about 60% to about 70%, at least about 45%, at least about 50%, at least about 55%, at least about 60%, at least about 65%, or at least about 70% of the total amount of active agent (e.g., midodrine hydrochloride) in the composition is released within about 2 hours after the start of the dissolution test. In a further embodiment, about 55% to about 85%, about 55% to about 80%, about 55% to about 77%, about 58% to about 77%, about 70% to about 80%, about 75% to about 85%, at least about 55%, at least about 60%, at least about 65%, at least about 70%, at least about 75%, at least about 80%, or at least about 85% of the total amount of active agent in the composition is released within about 4 hours after the start of the dissolution test. In another embodiment, about 65% to about 90%, about 65% to about 87%, about 65% to about 85%, at least about 80% to about 90%, at least about 65%, at least about 70%, at least about 75%, at least about 80%, at least about 85%, or at least about 90% of the total amount of active agent in the composition is released within about 6 hours after the start of the dissolution test. In another embodiment, at least about 70%, at least about 80%, at least about 85%, at least about 90%, or at least about 95% of the total amount of active agent in the composition is released within about 8 hours after the start of the dissolution test. In another embodiment, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or all of the total amount of active agent in the composition is released within about 9 hours, about 9.5 hours, about 10 hours, about 10.5 hours, about 11 hours, or about 11.5 hours after the start of the dissolution test. In another embodiment, at least about 70%, at least about 75%, at least about 80%, at least about 85%, or at least about 90%, at least about 91%, at least about 92%, at least about 93%, at least about 94%, at least about 95%, at least about 96%, at least about 97%, at least about 98%, at least about 99%, or all of the total amount of active agent in the composition is released within 12 hours, 12.5 hours, 13 hours, 13.5 hours, 14 hours, 14.5 hours, 15 hours, 15.5 hours or 16 hours after the start of the dissolution test.

In some embodiments, the extended release portion releases the remaining total amount of the active agent (e.g., midodrine hydrochloride) in the pharmaceutical composition at a slower rate than the release rate of the fast release portion. In some embodiments, a second rise in the active agent release rate, measured with an in vitro dissolution test, does not occur after 2 hours, after 2.5 hours, after 3 hours, after 3.5 hours, after 4 hours, after 4.5 hours, after 5 hours, after 5.5 hours, or after 6 hours from the start of the dissolution test. In another embodiment, the second rise does not occur between about 4 to about 16 hours, between about 4 to about 15 hours, between about 4 to about 14 hours, between about 4 to about 14 hours, between about 4 to about 12 hours, between about 4 to about 11 hours, between about 4 to about 10 hours, between about 4 to about 9 hours, between about 4 to about 8 hours, between about 4.5 to about 16 hours, between about 4.5 to about 15 hours, between about 4.5 to about 14 hours, between about 4.5 to about 13 hours, between about 4.5 to about 12 hours, between about 4.5 to about 11 hours, between about 4.5 to about 10 hours, between about 4.5 to about 9 hours, between about 4.5 to about 8 hours, between about 5 to about 16 hours, between about 5 to about 15 hours, between about 5 to about 14 hours, between about 5 to about 13 hours, between about 5 to about 12 hours, between about 5 to about 11 hours, between about 5 to about 10 hours, between about 5 to about 9 hours, between about 5 to about 8 hours, between about 6 to about 16 hours, between about 6 to about 15 hours, between about 6 to about 14 hours, between about 6 to about 13 hours, between about 6 to about 12 hours, between about 6 to about 11 hours, between about 6 to about 10 hours, between about 6 to about 9 hours, or between about 6 to about 8 hours after the start of the dissolution test.

In some embodiments, a second rise in the active agent release rate, measured with an in vitro dissolution test, does occur after 2 hours, after 2.5 hours, after 3 hours, after 3.5 hours, after 4 hours, after 4.5 hours from the start of the dissolution test, but does not occur after 5 hours from the start of the dissolution test. In another embodiment, the second rise does occur between about 3 to about 5 hours, between about 3 to about 4.5 hours, between about 3.5 to about 4.5 hours, or between about 4 to about 4.5 hours after the start of the dissolution test.

In some embodiments, the release rate of the active agent (e.g., midodrine HCl) does not substantially decrease during the extended release period where, for example, the decrease in release rate of the extended release portion is less than the decrease in release rate of the fast release portion (e.g., taking place about 15 min to about 1 hour after the start of an in vitro dissolution test). In some embodiments, the release rate of the active agent (e.g., midodrine HCl) decreases during the extended release period less than about 10%/hr, less than about 9%/hr, less than about 8%/hr, less than about 7%/hr, less than about 6%/hr, less than about 5%/hr, less than about 4%/hr, or less than about 3%/hr between about 1 hour to about 16 hours, about 1 hour to about 15 hours, about 1 hour to about 14 hours, about 1 hour to about 13 hours, about 1 hour to about 12 hours, about 1 hour to about 11 hours, about 1 hour to about 10 hours, about 1 hour to about 9 hours, about 1 hour to about 8 hours, about 1.5 hours to about 12 hours, about 1.5 hours to about 11 hours, about 1.5 hours to about 10 hours, about 1.5 hours to about 9 hours, about 1.5 hours to about 8 hours, about 2 hours to about 12 hours, about 2 hours to about 11 hours, about 2 hours to about 10 hours, about 2 hours to about 9 hours, about 2 hours to about 8 hours, about 2.5 hours to about 12 hours, about 2.5 hours to about 11 hours, about 2.5 hours to about 10 hours, about 2.5 hours to about 9 hours, about 2.5 hours to about 8 hours, about 3 hours to about 12 hours, about 3 hours to about 11 hours, about 3 hours to about 10 hours, about 3 hours to about 9 hours, about 3 hours to about 8 hours, about 4 hours to about 12 hours, about 4 hours to about 11 hours, about 4 hours to about 10 hours, about 4 hours to about 9 hours, or about 4 hours to about 8 hours after the start of an in vitro dissolution test.

In some embodiments, the pharmaceutical compositions disclosed herein allow for in vivo release of an active agent (e.g., midodrine hydrochloride) for up to about 16 hours, up to about 15 hours, up to about 14 hours, up to about 13 hours, up to about 12 hours, up to about 11 hours, up to about 10 hours, up to about 9 hours, or up to about 8 hours after administration to a subject, and can be characterized by (i) a first phase comprising a peak plasma concentration of desglymidodine and (ii) a second phase comprising a therapeutically effective plasma concentration of desglymidodrine. In some embodiments, the plasma concentration of desglymidodrine in the second phase remains steady or lower than the first phase peak plasma concentration. In some embodiments, the second phase comprises a second rise in plasma concentration of desglymidodrine around about 2 hours to about 4.5 hours after administration of the pharmaceutical composition to the subject. In some embodiments, the second phase does not comprise a second rise in plasma concentration of desglymidodrine after 5 hours (e.g., no second rise takes place 5-10 hours) after administration of the pharmaceutical composition to the subject. In some embodiments, the second phase comprises a third rise in plasma concentration of desglymidodrine at least about 6 hours after administration of the pharmaceutical composition to the subject. In some embodiments, the first phase peak plasma concentration of desglymidodrine is at least 10 ng/mL, at least 11 ng/mL, at least 12 ng/mL, at least 13 ng/mL, or at least 14 ng/mL. In some embodiments, the plasma concentration of desglymidodrine is maintained at a level of at least 7 ng/mL, at least 8 ng/mL, at least 9 ng/mL, at least 10 ng/mL, at least 11 ng/mL, at least 12 ng/mL, at least 13 ng/mL, or at least 14 ng/mL for at least 6 hours, at least 7 hours, at least 8 hours, at least 9 hours, or at least 10 hours after administration of the pharmaceutical composition to the subject.

In some embodiments, the pharmaceutical compositions disclosed herein can be characterized by a release profile comprising (i) a first phase which is a fast release of the active agent (e.g., midodrine HCl) and (ii) a second phase which is an extended release of the active agent, after administration to a subject.

In some embodiments, the first phase of the in vivo release profile can be characterized by a release of up to about 20%, up to about 30%, up to about 35%, up to about 40%, up to about 45%, up to about 50%, or up to about 55% (w/w) of the total amount of active agent in the composition within about 30 minutes, about 45 minutes, about 1 hour, about 90 minutes, about 2 hours, about 15 minutes to about 2 hours, about 30 minutes to about 2 hours, about 30 minutes to about 90 minutes, or about 30 minutes to 60 minutes after administration of the composition to a subject.

In some embodiments, the second phase of the in vivo release profile can be characterized by about 45%, about 50%, about 55%, about 60%, about 65%, about 70%, or about 85% (w/w) or less of the total active agent in the composition being released over an extended period of about 30 minutes to about 16 hours, about 45 minutes to about 16 hours, about 1 hour to about 16 hours, about 90 minutes to about 16 hours, about 2 hours to about 16 hours, about 30 minutes to about 14 hours, about 45 minutes to about 14 hours, about 1 hour to about 14 hours, about 90 minutes to about 14 hours, about 2 hours to about 14 hours, about 30 minutes to about 12 hours, about 45 minutes to about 12 hours, about 1 hour to about 12 hours, about 90 minutes to about 12 hours, about 2 hours to about 12 hours, about 30 minutes to about 10 hours, about 45 minutes to about 10 hours, about 1 hour to about 10 hours, about 90 minutes to about 10 hours, about 2 hours to about 10 hours, about 30 minutes to about 8 hours, about 45 minutes to about 8 hours, about 1 hour to about 8 hours, about 90 minutes to about 8 hours, or about 2 hours to about 8 hours after administration. In other embodiments, the second phase of the in vivo release profile can be characterized by about 45%, about 50%, about 55%, about 60%, about 65%, about 70%, or about 85% (w/w) or less of the total active agent in the composition being released over an extended period of about 30 minutes to about 12 hours, about 45 minutes to about 12 hours, about 1 hour to about 12 hours, about 90 minutes to about 12 hours, or about 2 hours to about 12 hours after administration. In other embodiments, the second phase of the in vivo release profile can be characterized by about 45%, about 50%, about 55%, about 60%, about 65%, about 70%, or about 85% (w/w) or less of the total active agent in the composition being released over an extended period lasting until about 8 hours to about 16 hours, about 8 hours to about 14 hours, about 8 hours to about 12 hours, about 8 hours to about 10 hours, or about 6 hours to about 8 hours after administration. In some embodiments, the in vivo release profile can be characterized by:

(i) about 20% to about 45%, about 20% to about 40%, about 20% to about 30%, about 25% to about 40%, about 25% to about 35%, or about 30% to about 40% w/w of the total amount of the active agent formulated to be released within about 1 hour after administration of the pharmaceutical composition; and (ii) the remaining total amount of the active agent formulated to be released over a period of about 6-12 (e.g., about 8-10) hours after administration of the pharmaceutical composition.

In some embodiments, the first phase is relatively fast and the second phase is steady or slower than the first phase with no second rise taking place 5-10 hours (e.g., after about 5 hours, about 5.5 hours, about 6 hours, about 6.5 hours, about 7 hours, about 7.5, or about 8 hours) following administration of the pharmaceutical composition to a subject. In some embodiments, the first phase is relatively fast and the second phase is steady or slower than the first phase with no second rise taking place between about 4.5 to about 16 hours, between about 4.5 to about 15 hours, between about 4.5 to about 14 hours, between about 4.5 to about 13 hours, between about 4.5 to about 12 hours, between about 4.5 to about 11 hours, between about 4.5 to about 10 hours, between about 4.5 to about 9 hours, between about 4.5 to about 8 hours, between about 5 to about 16 hours, between about 5 to about 15 hours, between about 5 to about 14 hours, between about 5 to about 13 hours, between about 5 to about 12 hours, between about 5 to about 11 hours, between about 5 to about 10 hours, between about 5 to about 9 hours, between about 5 to about 8 hours, between about 6 to about 16 hours, between about 6 to about 15 hours, between about 6 to about 14 hours, between about 6 to about 13 hours, between about 6 to about 12 hours, between about 6 to about 11 hours, between about 6 to about 10 hours, between about 6 to about 9 hours, or between about 6 to about 8 hours after administration of the pharmaceutical composition to a subject.

In some embodiments, the release rate of the active agent (e.g., midodrine HCl) in the extended release portion of a pharmaceutical composition provides a second rise in plasma concentration of desglymidodrine around about 2 to about 4.5 hours after administration of the pharmaceutical composition to the subject. In some embodiments, the extended release portion does not provide a second rise in plasma concentration of desglymidodrine 5 hours (e.g., no second rise taking place 5-10 hours) after administration of the pharmaceutical composition to the subject. In some embodiments, the extended release portion provides a third rise in plasma concentration of desglymidodrine at least about 6 hours after administration of the pharmaceutical composition to the subject.

In some embodiments, the fast release portion of an extended release composition of about 15 mg provides a first phase peak plasma concentration of desglymidodrine of at least 12 ng/mL, at least 13 ng/mL, or at least 14 ng/mL within about 1 hour. In some embodiments, fast release portion of an extended release composition of about 7.5 mg provides a first phase peak plasma concentration of desglymidodrine of at least 7 ng/mL within about 1 hour. In some embodiments, fast release portion of an extended release composition of about 30 mg provides a first phase peak plasma concentration of desglymidodrine of at least 24 ng/mL within about 1 hour. In some embodiments, the pharmaceutical composition provides a plasma concentration of desglymidodrine of at least 7 ng/mL, at least 8 ng/mL, at least 9 ng/mL, at least 10 ng/mL, at least 11 ng/mL, or at least 12 ng/mL for at least 6 hours, at least 7 hours, at least 8 hours, at least 9 hours, or at least 10 hours after administration of the pharmaceutical composition to the subject.

Methods of Use

The present disclosure provides methods of using the pharmaceutical compositions disclosed herein. Some aspects of the disclosure are directed to a method of treating or reducing the incidence of orthostatic hypotension in a human subject in need thereof comprising administering to the subject a pharmaceutical composition described herein. In some embodiments, the pharmaceutical compositions disclosed herein increases systolic blood pressure measured one minute after standing. In some embodiments, the composition is administered once a day. In some embodiments, the pharmaceutical composition maintains blood pressure of the subject within desired levels throughout the day, e.g., greater than 90 mmHg systolic and greater than 60 mmHg diastolic, e.g., about 120/80 mmHg.

The pharmaceutical compositions of the present disclosure can be used to treat or reduce the incidence of a disorder including at least one of: orthostatic hypotension; postural orthostatic tachycardia syndrome (POTS); dysautonomia; symptoms of chronic orthostatic hypotension corresponding to autonomic failure associated with Bradbury-Eggleston syndrome, Shy-Drager syndrome, diabetes mellitus disease, and Parkinson's disease; and retrograde ejaculation. In some embodiments, the pharmaceutical compositions of the present disclosure can be used to treat orthostatic hypotension in a subject suffering from Parkinson's disease. In some embodiments, the pharmaceutical compositions of the present disclosure can be used to treat a subject suffering from or at risk of suffering from postural orthostatic tachycardia syndrome (POTS).

In certain aspects, the method is directed to treating a subject suffering from or at risk of suffering from orthostatic hypotension due to autonomic failure comprising administering an effective amount of the pharmaceutical composition disclosed herein to a subject in need thereof. In some embodiments, the subject suffers from Bradbury-Eggleston, Shy-Drager syndromes, diabetes mellitus disease, or Parkinson's disease.

In certain aspects, the method is directed to treating a subject having Parkinson's disease who suffers from or is at risk of suffering from orthostatic hypotension comprising administering an effective amount of a pharmaceutical composition disclosed herein to a subject in need thereof.

In certain aspects, the method is directed to treating a subject having postural orthostatic tachycardia syndrome (POTS) who suffers from or is at risk of suffering from orthostatic hypotension comprising administering an effective amount of a pharmaceutical composition disclosed herein to a subject in need thereof.

In some embodiments, the subject is 10-50 years old, 10-25 years old, e.g., 13-18 years old, 13-21 years old, or 13-25 years old. In some embodiments, the subject is male or female. In some embodiments, the subject is male. In some embodiments, the subject is female. In some embodiments, the subject is female, aged 13-25 years old and suffers from POTS. In some embodiments, the subject suffers from Parkinson's disease. In some embodiments, the subject suffers from early-onset Parkinson's disease (e.g., is 50 years old or younger). In some embodiments, the subject is older than 50 years.

The method of treatment can include administering a single dose of a pharmaceutical composition disclosed herein to a subject. The administration can be effective to cause a fast release (e.g., within 2 hours, 90 minutes, 1 hour, 45 minutes, 30 minutes, or 15 minutes) of the active agent into the subject's plasma and an extended release (e.g, for at least 8 hours, at least 10 hours, at least 12 hours, or at least 14 hours) of the active agent into the subject's plasma. The active agent can include one or more of: midodrine, a pharmaceutically acceptable salt of midodrine, desglymidodrine, a pharmaceutically acceptable salt of desglymidodrine, or a combination thereof.

In some embodiments, the method comprises administering a total single daily dose of a pharmaceutical composition disclosed herein which is greater than a corresponding total daily dose of an immediate release tablet given three times daily, e.g., a single 20 mg dose of a pharmaceutical composition disclosed herein can be administered in place of three times daily administration of a 5 mg immediate release tablet (i.e., a 15 mg dose IR total daily dose). In some embodiments, the 20 mg dose is a multi-layer tablet (e.g., a bi-layer or tri-layer tablet) comprising a fast release portion and an extended release portion.

In some embodiments, the single dose can be administered to effectively raise blood pressure (e.g., to at least 12 ng/mL or at least 14 ng/mL) in the subject during the fast release period and maintain the blood pressure (e.g., at a level of at least 7 ng/mL, at least 8 ng/mL, at least 9 ng/mL, or at least 10 ng/mL) in the subject during the extended release period. The single dose can include the active agent in an amount in milligrams of about: 5, 5.5, 6, 6.5, 7, 7.5, 8, 8.5, 9, 9.5, 10, 12.5, 15, 17.5, 20, 22.5, 25, 27.5, 30, 32.5, 35, 37.5, 40, 42.5, 45, 47.5, 50, 52.5, 55, 57.5, 60, 62.5, 65, 67.5, 70, 72.5, 75, 77.5, 80, 90, 100, 110, 120, 130, 140, and 150, e.g., about 10 mg, about 15 mg, about 20 mg, about 30 mg, about 45 mg, or a range between about 5 mg to about 150 mg, between about 5 mg to about 120 mg, between about 5 mg to about 100 mg, between about 5 mg to about 75 mg, between about 10 to about 70 mg, between about 4 mg to about 50 mg, or between about 18 mg to about 25 mg.

In some embodiments, the pharmaceutical composition is an oral suspension and the dosage can be titrated to an effective level for the subject. A subject can start with an initial dose of the active and the subsequent doses can be adjusted based on the subject's response to the initial dose. Dose titration can be conveniently achieved for an oral suspension dosage form by adjusting the volume of oral suspension to be administered to the subject.

In some embodiments, the methods of the present application allow the active agent (e.g., midodrine hydrochloride) to be given less frequently than an immediate release dosage and still maintain blood pressure in a clinically acceptable range, e.g., greater than 90 mmHg systolic and greater than 60 mmHg diastolic, e.g., about 120/80 mmHg, throughout the day.

The method can include administering a single dose to a subject according to any aspect of the pharmaceutical composition described herein. For example, the method can include administering a single dose to the subject in a dosage form including at least one of: a multilayer tablet, e.g., a bi-layer tablet or a tri-layer tablet, comprising a fast release and extended release layers; an extended release core coated with a fast release coating; a combined fast release and extended release tablet; a plurality of particulates that comprise a population of fast release and a population of extended release, the plurality of particulates configured for dispersal in a liquid carrier (or a suspending vehicle) suitable for oral administration; or a plurality of multi-particulates (e.g., particles, granules, beads, spheres, or mini-tablets) pellets that are a population of fast release and a population of extended release. The method further can include combining the plurality of particulates (e.g., multi-particulates disclosed herein) with a liquid followed by oral administration to the subject; and the plurality of particulates (e.g., multi-particulates disclosed herein) dispersed in a liquid carrier suitable for oral administration.

In some embodiments, the method can include administering the single dose to the subject such that the extended release of the active agent into the subject's plasma over the extended release period is characterized by an extended release rate. The method can include administering the single dose to the subject such that greater than about 50% (w/w) of the active agent in the pharmaceutical composition is released to the subject over the extended release period. The extended release period can be, in hours, at least one of, or at least about one of: 4, 5, 6, 7, 8, 9, 10, 11, 12, 13, 14, 15, or 16 hours, e.g., about 12 hours, or a range between any two of the preceding values, for example, of between about 4 hours and about 12 hours, between 6 hours to 12 hours, between 8 hours to 12 hours, between 8 hours to 14 hours, or between 8 hours to 16 hours.

In one embodiment, the pharmaceutical composition, e.g., a tablet, a capsule, or a suspension, disclosed herein is administered once or twice daily to a human subject in need thereof. In another embodiment, the pharmaceutical composition is administered once daily to a human subject in need thereof. The dose administered may be sufficient to obtain a suitable therapeutic response in the subject.

In one embodiment, this disclosure provides a method of treating orthostatic hypotension in a human subject in need thereof comprising administering to the human subject a pharmaceutical composition comprising:

a fast release portion comprising about 1.5 mg to about 45 mg (e.g., about 2 mg to about 25 mg, about 4 mg to about 20 mg, about 4 mg to about 15 mg, or about 5 mg to about 10 mg) of an active agent selected from the group consisting of midodrine, a pharmaceutically acceptable salt of midodrine, desglymidodrine, a pharmaceutically acceptable salt of desglymidodrine, and a combination thereof, and an extended release portion comprising about 3.5 mg to about 105 mg (e.g., about 4 mg to about 75 mg, about 5 mg to about 50 mg, about 5 mg to about 25 mg, about 5 mg to about 20 mg, about 7.5 mg to about 15 mg, or about 10 mg to about 15 mg) of an active agent selected from the group consisting of midodrine, a pharmaceutically acceptable salt of midodrine, desglymidodrine, a pharmaceutically acceptable salt of desglymidodrine, and a combination thereof.

In some embodiments, the pharmaceutical composition has an in vitro dissolution release profile such that up to about 20%, up to about 30%, up to about 35%, up to about 40%, up to about 45%, up to about 50%, or up to about 55% (w/w) of the total amount of active agent in the composition is released within 1 hour, and at least about 95% of the total amount of active agent in the composition is released within 8, 10, 12, 14, or 16 hours.

In other embodiments, the method comprises administering a pharmaceutical composition comprising:

a fast release portion comprising about 1.5 mg to about 45 mg (e.g., about 2 mg to about 25 mg, about 4 mg to about 20 mg, about 4 mg to about 15 mg, or about 5 mg to about 10 mg) of midodrine hydrochloride, a binder, a glidant, and a lubricant, wherein the midodrine HCl is present in an amount of up to 40%, up to 35%, up to 30%, up to 25%, about 2% to about 30%, about 2% to about 20%, or about 2% to about 10% of the total weight of the fast release portion; and an extended release portion comprising about 3.5 mg to about 105 mg (e.g., about 4 mg to about 75 mg, about 5 mg to about 50 mg, about 5 mg to about 25 mg, about 5 mg to about 20 mg, about 7.5 mg to about 15 mg, or about 10 mg to about 15 mg) of midodrine HCl and a rate controlling agent, wherein the midodrine HCl is present in an amount of up to 60%, up to 65%, up to 70%, up to 75%, up to 80%, about 2% to about 30%, about 2% to about 20%, or about 2% to about 10% of the total weight of the extended release portion, and the midodrine HCl to rate controlling agent weight ratio is about 1:1 to about 1:30.

In some embodiments, the fast release portion comprises about 1% to about 40%, about 2% to about 40%, about 2% to about 20%, about 2% to about 15%, about 2% to about 10%, about 2% to about 5%, about 3% to about 15%, about 3% to about 10%, about 3% to about 10%, or about 3% to about 5% of midodrine HCl of the total weight of the fast release portion. In some embodiments, the fast release portion comprises about 1%, 2%, 3%, 4%, 5%, 6%, 7%, 8%, 9%, or 10% of midodrine HCl of the total weight of the fast release portion.

In some embodiments, the extended release portion comprises about 2% to about 20%, about 2% to about 15%, about 2% to about 10%, about 3% to about 15%, about 3% to about 10%, about 3% to about 5%, about 4% to about 10%, about 4% to about 8%, or about 4% to about 6% of midodrine HCl of the total weight of the extended release portion. In some embodiments, the extended release portion comprises about 1%, 2%, 3%, 4%, 5%, 6%, 7%, 8%, 9%, 10%, 11%, 12%, 13%, 14%, 15%, 16%, 17%, 18%, 19%, or 20% of midodrine HCl of the total weight of the extended release portion. In some embodiments, the weight ratio of the midodrine HCl in the extended release portion to the rate controlling agent in the extended release portion is about 1:1 to about 1:20, about 1:1 to about 1:10, about 1:1 to about 1:8, about 1:1 to about 1:7, about 1:1 to about 1:6, or about 1:1 to about 1:5. In some embodiments, the weight ratio of the midodrine HCl in the extended release portion to the rate controlling agent in the extended release portion is about 1:1, 1:2, 1:3, 1:4, 1:5, 1:6, 1:7, 1:8, 1:9, or 1:10.

In some embodiments, the fast release portion comprises about 2% to about 10% or about 3% to about 5% of midodrine HCl of the total weight of the fast release portion, the extended release portion comprises about 2% to about 15% or about 4% to about 6% of midodrine HCl of the total weight of the extended release portion, and the weight ratio of the midodrine HCl in the extended release portion to the rate controlling agent in the extended release portion is about 1:4 to about 1:5.

In some embodiments, the method is directed to administering a pharmaceutical composition with a fast release portion and an extended release portion, wherein both the fast release and the extended release portions both comprise an active agent (e.g., midodrine hydrochloride). In some embodiments, the active agent in the fast release portion is released within about 60 minutes, about 50 minutes, about 45 minutes, about 40 minutes, about 35 minutes, about 30 minutes, about 25 minutes, about 20 minutes, about 15 minutes, about 10 minutes, or about 5 minutes after the start of an in vitro dissolution test. In some embodiments, the active agent in the fast release portion is released within about 90 minutes, about 60 minutes, about 50 minutes, about 45 minutes, about 40 minutes, about 35 minutes, about 30 minutes, about 25 minutes, about 20 minutes, about 15 minutes, about 10 minutes, or about 5 minutes after administration to a subject. In some embodiments, at least a portion of the active agent is released over a time period of about 1 hour to about 16 hours, about 1 hour to about 15 hours, about 1 hour to about 14 hours, about 1 hour to about 13 hours, about 1 hour to about 12 hours, about 1 hour to about 11 hours, or 1 hour to about 10 hours after the start of an in vitro dissolution test. In some embodiments, at least a portion of the active agent is released over a time period of about 1 hour to about 16 hours, about 1 hour to about 15 hours, about 1 hour to about 14 hours, about 1 hour to about 13 hours, about 1 hour to about 12 hours, about 1 hour to about 11 hours, or 1 hour to about 10 hours after administration to a subject.

In some embodiments, administration of the pharmaceutical composition results in a maximum plasma concentration ($C_{max}$) of midodrine hydrochloride or its active metabolite desglymidodrine in the range of about 2 ng/mL to about 100 ng/mL, about 2 ng/mL to about 50 ng/mL, about 2 ng/mL to about 25 ng/mL, about 2 ng/mL to about 15 ng/mL, or about 2 ng/mL to about 10 ng/mL after oral administration of the pharmaceutical composition to a subject. In one embodiment, administration of the pharmaceutical composition can result in the plasma level of the active metabolite, desglymidodrine, in a subject of at least 3 ng/mL, at least 4 ng/mL, at least 5 ng/mL, at least 6 ng/mL, at least 7 ng/mL, at least 8 ng/mL, at least 9 ng/mL, at least 10 ng/mL, at least 11 ng/mL, at least 12 ng/mL, at least 13 ng/mL, at least 14 ng/mL, at least 15 ng/mL, or at least 14 ng/mL for a duration of at least about 2 hours, at least about 4 hours, at least about 6 hours, at least about 8 hours, at least about 12 hours, or at least about 16 hours.

In some embodiments, the methods of the application are directed to a multilayer tablet, a capsule, a suspension, or other dosage forms of the pharmaceutical compositions disclosed herein, which are used to treat orthostatic hypotension in a subject. In some embodiments, the method can comprise the step of providing a bi-layer tablet or tri-layer tablet with a fast release layer comprising the active agent (e.g., midodrine hydrochloride) in an amount that ranges from about 1.5 mg to 45 mg (e.g., about 4 mg to about 75 mg, about 5 mg to about 50 mg, about 5 mg to about 25 mg, about 5 mg to about 20 mg, about 7.5 mg to about 15 mg, or about 10 mg to about 15 mg), and an extended release layer comprising the active agent (e.g., midodrine HCl) in an amount that ranges from about 3.5 mg to about 105 mg (e.g., about 2 mg to about 25 mg, about 4 mg to about 20 mg, about 4 mg to about 15 mg, or about 5 mg to about 10 mg). The fast release layer of the tablet can also be configured to release up to about 20%, up to about 30%, up to about 35%, up to about 40%, up to about 45%, up to about 50%, or up to about 55% (w/w) of the active agent within about 1 hour in an in vitro dissolution test. The extended release layer or layers can be configured to release the remaining amount of the active agent over a prolonged duration of about 1 hour to about 8 hours, about 1 hour to about 10 hours, about 1 hour to about 12 hours or about 1 hour to about 16 hour after start of the dissolution test.

Dosage

The pharmaceutical compositions disclosed herein can be administered once or twice daily to a human subject in need thereof. In one embodiment, the pharmaceutical formulation is a tablet that can be administered once daily to a human subject in need thereof. The dose administered can be effective to cause a desired therapeutic and/or prophylactic response in the subject. In some embodiments, the pharmaceutical composition comprises a dose of about 5 mg to about 150 mg, about 5 mg to about 120 mg, about 7.5 to about 150 mg, about 7.5 mg to about 120 mg, about 5 mg to about 100 mg, about 7.5 mg to about 100 mg, about 7.5 mg to about 75 mg, about 7.5 mg to about 50 mg, about 10 mg to about 100 mg, about 15 mg to about 100 mg, about 20 mg to about 100 mg, about 10 mg to about 75 mg, about 10 mg to about 50 mg, about 15 mg to about 75 mg, about 15 mg to about 50 mg, about 20 mg to about 75 mg, about 20 mg to about 50 mg, about 18 mg to about 25 mg, or about 20 to about 25 mg of an active agent (e.g., midodrine HCl), which is administered once or twice per day. In one embodiment, the pharmaceutical composition comprises about 5 mg, about 7.5 mg, about 10 mg, about 12.5 mg, about 15 mg, about 17.5 mg, about 18 mg, about 20 mg, about 22.5 mg, about 25 mg, about 27.5 mg, about 30 mg, about 32.5 mg, about 35 mg, about 37.5 mg, about 40 mg, about 42.5 mg, about 45 mg, about 47.5 mg, about 50 mg, about 60 mg, about 100 mg, about 120 mg, or about 150 mg of the active agent (e.g., midodrine HCl), which is administered once or twice per day.

In some embodiments, the pharmaceutical composition disclosed herein comprises a dosage form for once daily administration wherein the total amount of the active agent (e.g., midodrine HCl) in the dosage form is at least 10%, at least 15%, at least 20%, at least 25%, at least 30%, at least 40%, at least 45%, at least 50%, at least 60%, or at least 70%, more than the total amount of active agent (e.g., midodrine HCl) in three immediate release tablets (e.g., three 2.5 mg, 5 mg, or 10 mg IR tablets). In some embodiments, the dosage form for once daily administration comprises less than 70%, less than 60%, less than 50%, less than 45%, less than 40%, less than 35%, less than 30%, between 10-70%, between 10-55%, between 10-50%, between 10-40%, between 10-35%, between 10-30%, between 15-50%, between 15-40%, between 15-35%, between 15-30%, between 20-50%, between 20-40%, between 20-35%, between 20-30%, between 25-50%, between 25-40%, between 25-35%, between 25-30%, between 30-50%, between 30-45%, between 30-40%, about 10%, about 20%, about 30%, about 40%, about 50%, about 60%, about 70%, more active agent (e.g., midodrine HCl) than the total amount of active agent (e.g., midodrine HCl) in three immediate release tablets (e.g., three 2.5 mg, 5 mg, or 10 mg IR tablets). For example, a single 10 mg dosage form of a pharmaceutical composition disclosed herein can be administered once daily (total daily dose of 10 mg) in place of a 2.5 mg immediate release tablet given three times daily (total daily dose of 7.5 mg). A single 20 mg dosage form of a pharmaceutical composition disclosed herein can be administered once daily (total daily dose of 20 mg) in place of a 5 mg immediate release tablet given three times daily (total daily dose of 15 mg). A single 40 mg dosage form of a pharmaceutical composition disclosed herein can be administered once daily (total daily dose of 40 mg) in place of a 10 mg immediate release tablet given three times daily (total daily dose of 30 mg). In some embodiments, the 10 mg, 20 mg, or 40 mg dose for once daily administration is a multi-layer tablet (e.g., a bi-layer or tri-layer tablet) comprising a fast release portion and an extended release portion.

Methods of Making

In some aspects, the application is directed to making a pharmaceutical composition disclosed herein. In some embodiments, the pharmaceutical composition is prepared for oral delivery. In some embodiments, the pharmaceutical composition is a tablet, a capsule, an orally disintegrating tablet, a chewable tablet, a buccal adhesive tablet, a sublingual tablet, an oral suspension, or a powder, granules, or multi-particulates for oral suspension.

In certain embodiments, the methods of making comprise making a pharmaceutical composition comprising a multi-layer tablet (e.g., a bi-layer tablet or a tri-layer tablet) with fast release and extended release layers, a tablet with an extended release core and a fast release drug coating over the extended release core, a tablet-in-tablet with an extended release in a fast release tablet, a compression coated tablet having an extended release core and a fast release coat, a fast release core coated with an extended release coating followed by a fast release drug coating, a capsule filled with multi-particulates (e.g., pellets, particles, granules, beads, spheres, or mini-tablets) having an extended release core and fast release coating, a blend of fast and extended release multi-particulates compressed into a tablet, a blend of fast and extended release multi-particulates filled into a sachet for reconstitution, or an extended release osmotic controlled tablet with a fast release drug layer coating.

In some embodiments, the method for making the pharmaceutical composition comprises a drug layering dispersion comprising the active agent layered on to microcrystalline cellulose spheres in fluid bed processor by bottom spray method. A first portion (e.g., at least about 30%, at least about 40%, at least about 50%, at least about 60%, or about 70%) of the drug layered multi-particulates are coated with a rate controlling agent (e.g., ethylcellulose and oleic acid) to form a first extended release multi-particulate portion; a second portion (e.g., at least about 15%, at least about 20%, at least about 25%, or about 20%) of the drug layered multi-particulates are coated with a rate controlling agent (e.g., Eudragit® L 30D 55) to form a second extended release multi-particulate portion; and the fast release (uncoated drug layered multi-particulates), the first extended release multi-particulates, and the second extended release multi-particulates are lubricated (e.g., with Talc and Magnesium stearate) and filled in to capsules.

In some embodiments, the method for making the pharmaceutical composition comprises one or more of dry granulation, wet granulation, roller compaction, extrusion/spheronization, rotary pelletization, hot melt extrusion, fluid bed granulation, fluid bed coating, compression coating, powder coating, and the like.

Kit

In one embodiment, a kit is provided. In some embodiments, the kit comprise multi-particulates (e.g., pellets, particles, granules, beads, spheres, or mini-tablets) disclosed herein and a liquid vehicle, wherein the multi-particulates can be combined with a liquid vehicle to form a suspension. In some embodiments, the kit includes a first pharmaceutical composition and a second pharmaceutical composition, wherein the first and second pharmaceutical compositions comprise the same active agent or different active agents. In one embodiment, the first pharmaceutical composition comprises a fast release portion and an extended release portion, wherein both the fast release portion and the extended release portion include an active agent selected from the group consisting of midodrine, a pharmaceutically acceptable salt of midodrine, desglymidodrine, and a pharmaceutically acceptable salt of desglymidodrine. In one embodiment, the active agent is present in the fast release portion in the range of about 1.5 mg to 45 mg (e.g., about 4 mg to about 75 mg, about 5 mg to about 50 mg, about 5 mg to about 25 mg, about 5 mg to about 20 mg, about 7.5 mg to about 15 mg, or about 10 mg to about 15 mg), and the active agent is present in the extended release portion in a range of about 3.5 mg to about 105 mg (e.g., about 2 mg to about 25 mg, about 4 mg to about 20 mg, about 4 mg to about 15 mg, or about 5 mg to about 10 mg). In another embodiment, the fast release portion releases about 20% to about 55%, about 20% to about 50%, about 20% to about 45%, about 20% to about 40%, about 25% to about 40%, about 30% to about 50%, or about 30% to about 40% (e.g., 20-55%, 20-50%, 20-45%, 20-40%, 25-40%, 30-50%, or 30-40%) w/w of the total amount of active agent in the composition within about 1 hour, and the extended release portion releases the remaining total amount of active agent in the composition over about 1 hour to about 16 hours, about 1 to about 14 hours, about 1 to about 12 hours, about 1 to about 10 hours, or about 1 to about 8 hours.

In certain embodiments, the second composition can be a fast release composition comprising an active agent selected from the group consisting of midodrine, a pharmaceutically acceptable salt of midodrine, desglymidodrine, and a pharmaceutically acceptable salt of desglymidodrine. In one embodiment, the active agent is present in the range of 2.5 mg to 20 mg and releases substantially all of the active agent within about 1 hour of administration of the second composition to a subject. In another embodiment, the first composition and second composition are administered to a subject simultaneously. In yet another embodiment, the first composition and second composition are administered to a subject sequentially, wherein the second composition is administered after the first composition.

Combination Therapy

Certain aspects of the application are directed to a method for treating a subject comprising administering a pharmaceutical composition disclosed herein and a further pharmaceutical composition comprising an additional active agent. The additional active agent can be any active drug substance that can be beneficially used with midodrine, a pharmaceutically acceptable salt thereof, desglymidodrine, a pharmaceutically acceptable salt thereof, or combination thereof. Non-limiting examples of additional active agents are hydrocortisone, fludrocortisone, octreotide, and the like. In some embodiments, the pharmaceutical composition can be administered adjunctively with one or more pharmaceutical compositions containing other active agents, e.g., by simultaneous administration of the active agents in the same dosage form, simultaneous administration of the active agents in separate dosage forms, or separate administration of the active agents.

EXAMPLES

The disclosure is further illustrated by the following examples which are provided merely to be exemplary and do not limit the scope. Certain modifications and equivalents will be apparent to those skilled in the art and are intended to be included within the scope of the disclosure. The present disclosure provides, but is not limited to, the following formulation examples.

Example 1

Preparation and In Vitro Dissolution Testing of Midodrine HCl Bi-Layer Tablets

Midodrine hydrochloride bi-layer tablets (15 mg, 20 mg, 30 mg, and 45 mg) containing a fast release layer and an extended release layer were prepared using the components shown in TABLE 1. Midodrine HCl was blended with microcrystalline cellulose, and coloring agent. The blend was then lubricated using colloidal silicon dioxide and magnesium stearate. For the extended release layer, midodrine HCl, microcrystalline cellulose and hydroxy propyl cellulose were mixed and granulated using purified water. The granules were dried and lubricated using colloidal silicon dioxide and magnesium stearate. Fast release and extended release layers were compressed in to bi-layer tablets using a bi-layer tablet press.

TABLE 1

| Ingredient No. | Ingredient | Quantity (mg/tablet) 15 mg tablet | Quantity (mg/tablet) 20 mg tablet | Quantity (mg/tablet) 30 mg tablet | Quantity (mg/tablet) 45 mg tablet |
|---|---|---|---|---|---|
| Fast Release Layer | | | | | |
| 1 | Midodrine HCl | 5.00 | 6.67 | 10.00 | 15.00 |
| 2 | Microcrystalline cellulose | 142.75 | 141.08 | 137.75 | 132.75 |
| 3 | D&C Red 30 | 0.75 | 0.75 | 0.75 | 0.75 |
| 4 | Colloidal Silicon | 0.75 | 0.75 | 0.75 | 0.75 |
| 5 | Magnesium | 0.75 | 0.75 | 0.75 | 0.75 |
| | Total | 150.00 | 150.00 | 150.00 | 150.00 |
| Extended Release Layer | | | | | |
| 6 | Midodrine HCl | 10.00 | 13.34 | 20.00 | 30.00 |
| 7 | Microcrystalline cellulose | 182.00 | 178.66 | 172.00 | 162.00 |
| 8 | Hydroxy propyl cellulose | 105.00 | 105.00 | 105.00 | 105.00 |
| 9 | Colloidal Silicon | 1.50 | 1.50 | 1.50 | 1.50 |
| 10 | Magnesium | 1.50 | 1.50 | 1.50 | 1.50 |
| | Total | 300.00 | 300.00 | 300.00 | 300.00 |
| | TOTAL | 450.00 | 450.00 | 450.00 | 450.00 |

The in vitro dissolution tests for the bi-layer tablets of Example 1 were performed under the following conditions: USP Apparatus I (baskets) at 100 rpm in 900 mL at 37° C., 0-2 hours, 0.1N HCl (pH 1.2); 2-4 hours, acetate buffer (pH 4.5); 4-16 hours, phosphate buffer (pH 6.8). Similar dissolution profiles were observed in different buffers and agitation speeds (75 and 150 rpm). These results show that the drug release rate of midodrine is independent of simulated fast and fed dissolution conditions, and suggest an absence of food effect in vivo.

FIG. 1 shows the in vitro dissolution profiles for the tablets of TABLE 1. FIG. 1 shows that tablets containing 15 mg, 30 mg, and 45 mg of midodrine HCl demonstrate fast release of about 40% to 50% of active agent from the fast release layer within about 1 hour and an extended release of the remaining active agent over the test period of 12 hours.

Figure 2:
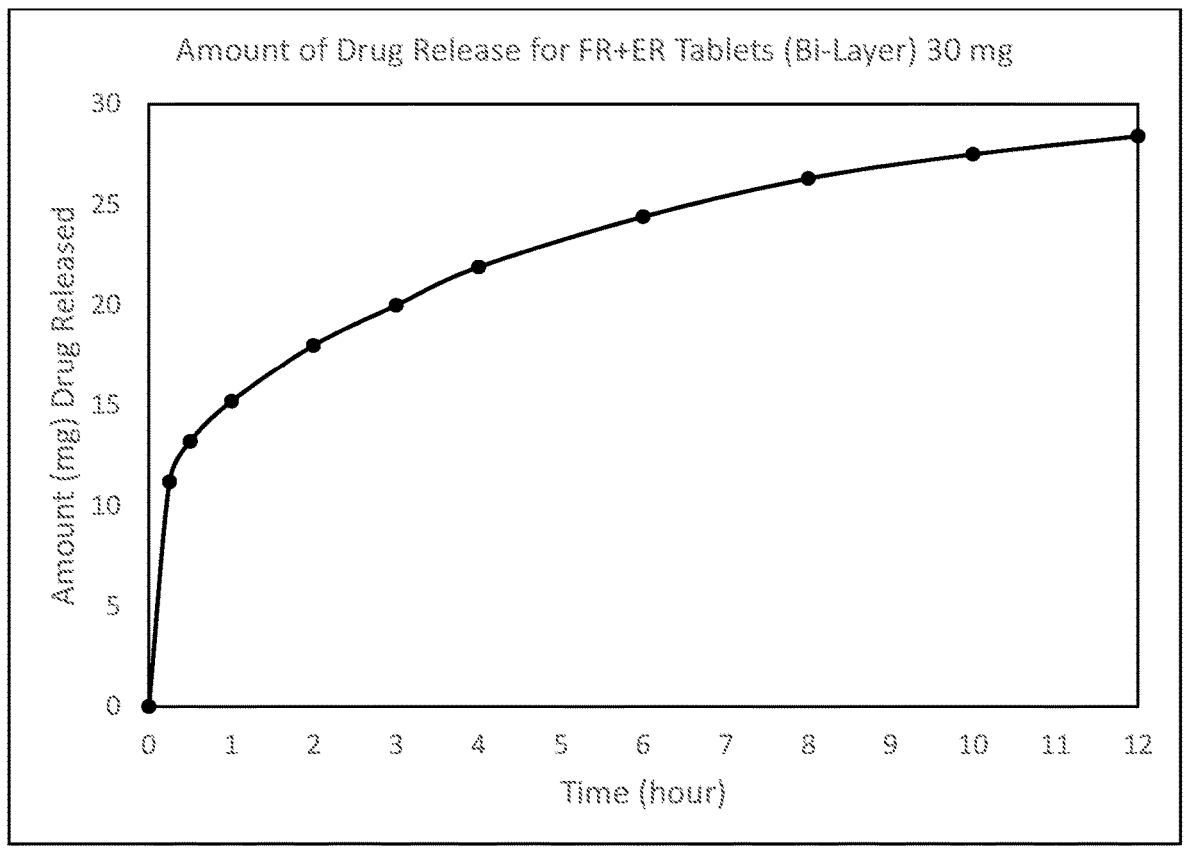
FIG. 2 is a graph that illustrates the in vitro dissolution profile (shown as amount (mg) of active agent released over a period of 12 hours) for a fast release/extended release bi-layer tablet formulation containing 30 mg of midodrine HCl.

The dissolution profile of the 30 mg midodrine HCl tablet is shown in FIG. 2. These data show that the fast release/extended release composition containing 30 mg of midodrine HCl shows a fast release of the active agent followed by an extended release of the active agent for at least 10 hours.

The in vitro dissolution data for the bi-layer tablets tested in Example 1 support the use of the disclosed pharmaceutical formulations in vivo for an effective fast release followed by a steady extended release period.

Example 2

Simulated Desglymidodrine Plasma Profiles

Figure 3:
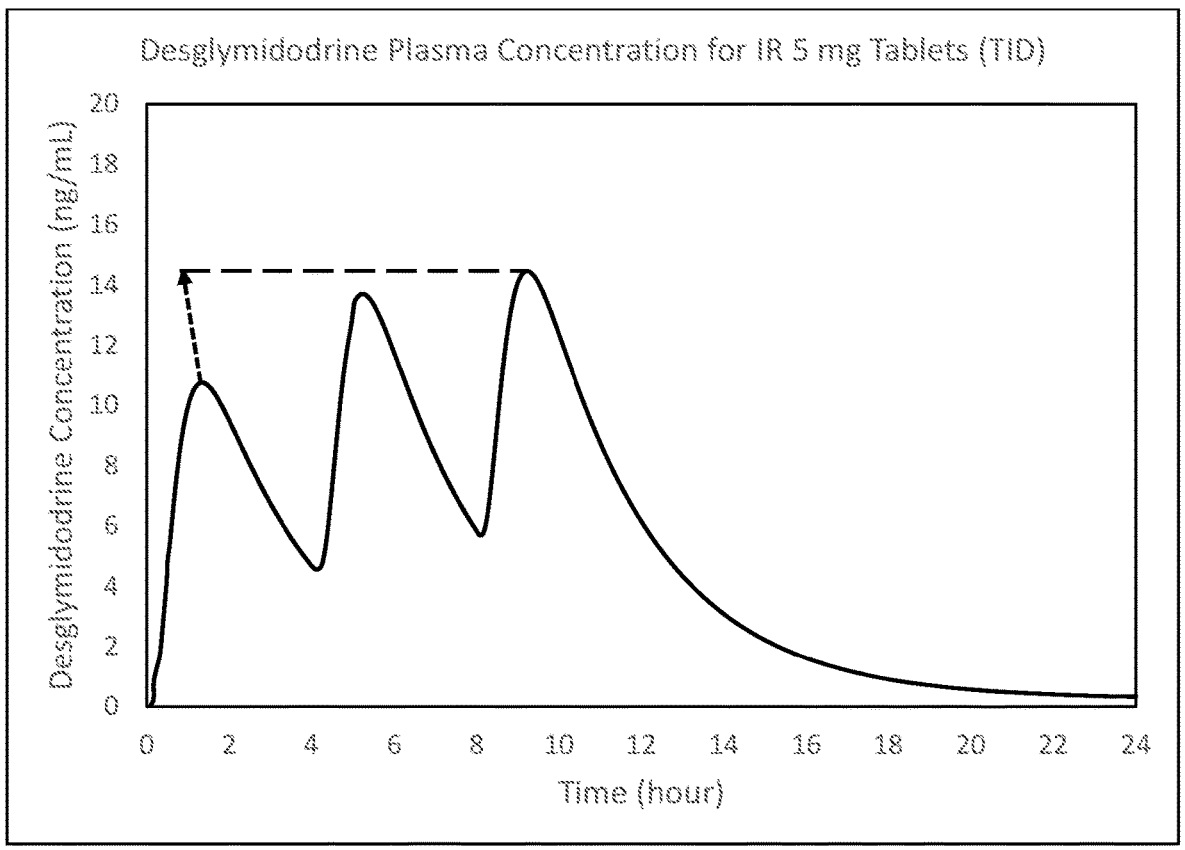
FIG. 3 shows a simulated 20 hour plasma concentration (ng/mL) profile of desglymidodrine (the active metabolite of midodrine HCl) after administration of 5 mg immediate release tablets at 0, 4, and 8 hours (i.e., a TID regimen).

Plasma profiles of desglymidodrine (the active metabolite of midodrine HCl) after administration of 5 mg immediate release tablets at 0, 4, and 8 hours (i.e., a TID regimen) were simulated using known modeling methods. The simulated desglymidodrine plasma concentration (ng/mL) v. time (h) for 5 mg immediate release tablets (TID) is shown in FIG. 3. It can be seen from the simulations that the first immediate release TID dose does not produce as high a level of desglymidodrine as the third immediate release TID dose. As shown in the simulation, desglymidodrine level increases with respective doses and reaches a maximum concentration (about 14 ng/mL) after administration of the third dose.

Figure 4:
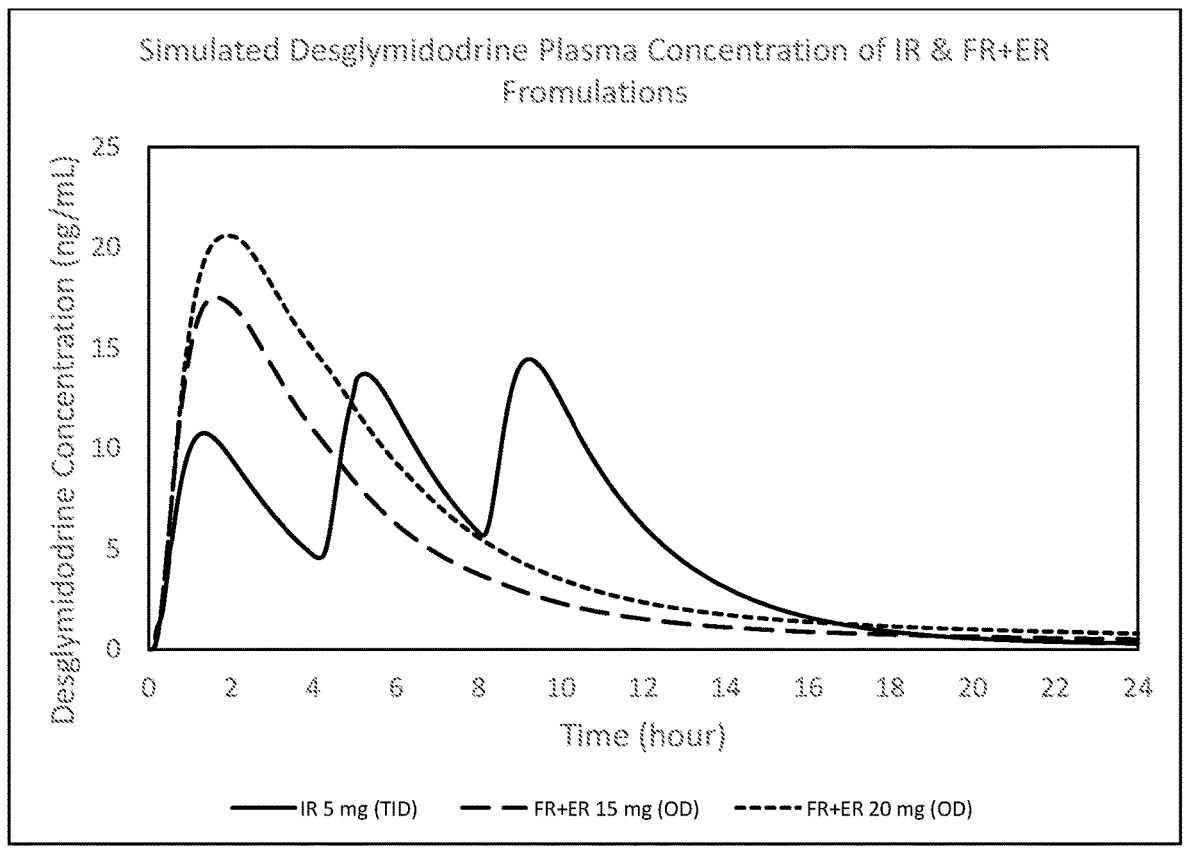
FIG. 4 shows a simulated 24 hour plasma concentration (ng/mL) profile of desglymidodrine (the active metabolite of midodrine HCl) for fast release/extended release 15 mg and 20 mg formulations of the present disclosure compared with a simulated plasma profile of TID immediate release 5 mg tablets.

The same modeling method was used to simulate the plasma profiles of desglymidodrine after administration of 15 mg and 20 mg fast release/extended release tablets (formulations shown in Table 1) of the present disclosure (FR+ER) compared to 5 mg immediate release tablets at 0, 4, and 8 hours (i.e., a TID regimen). The simulated desglymidodrine plasma concentration (ng/mL) v. time (h) for these formulations are shown in FIG. 4. As shown in FIG. 4, when the FR+ER 15 mg tablet was simulated and compared with a TID immediate release 5 mg tablets, it provides greater than 14 ng/mL desglymidodrine initially (within about 1 hour). Additional FR+ER formulation at higher strengths, i.e., 20 mg, also achieved this high initial peak desglymidodrine concentration (simulated). These FR+ER tablets showed a fast in vitro initial drug release (about 40% in 30 minutes) and no second rise after the initial release.

Example 3

Simulated Dissolution and Desglymidodrine Plasma Profiles 20 mg FR+ER formulation was designed as shown in Example 7 (Table 5), and the dissolution and plasma profiles were simulated for one time daily doses of these formulations. In short, the 20 mg formulation is prepared as an extended release tri-layer tablets containing fast and extended release layers.

Figure 5:
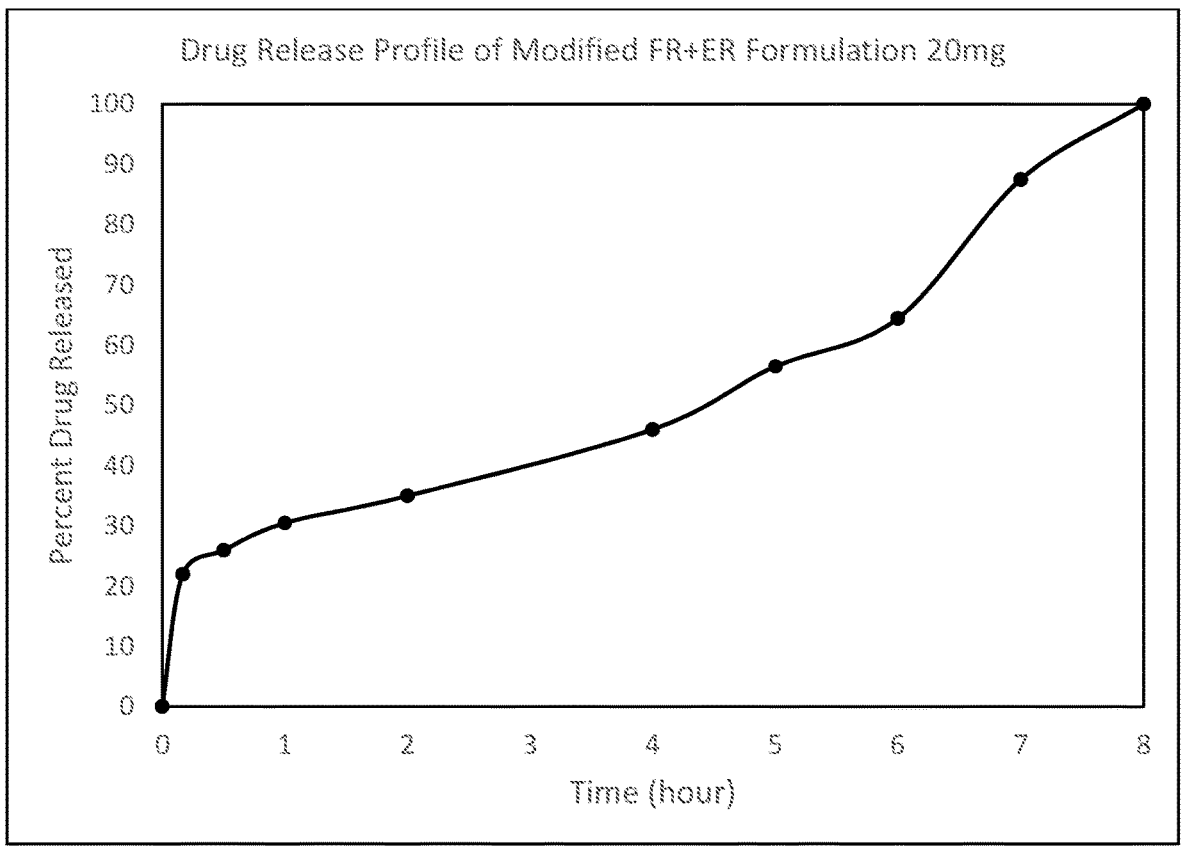
FIG. 5 shows simulated dissolution profiles (showing percent drug released over time) for 20 mg formulation of the present disclosure.

As shown in FIG. 5, the simulated dissolution profiles for the 20 mg FR+ER formulation, has an extended drug release phase of that provides a slow-steady release to fast second rise at about 2 to 4 hours and a third rise at about 6 hours. The simulated dissolution profiles also show drug release up to about 8 hours.

Figure 6:
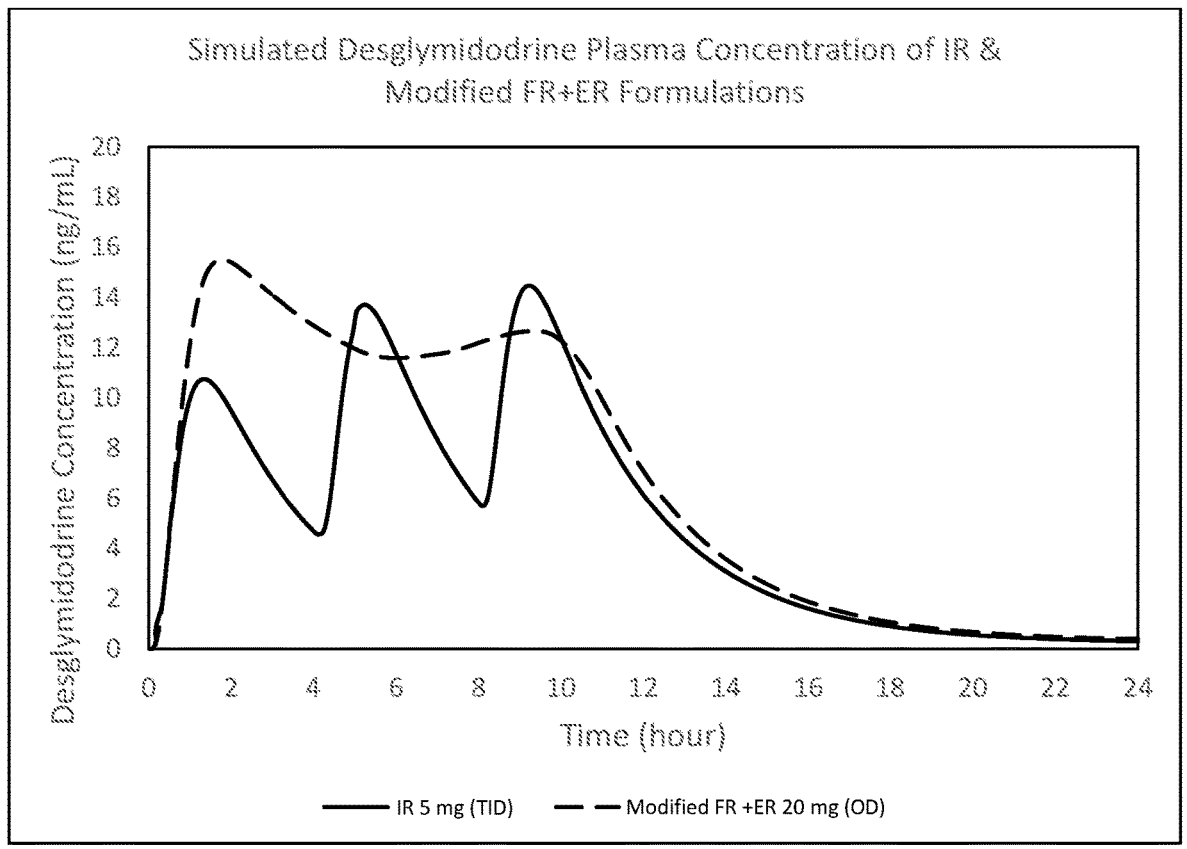
FIG. 6 shows simulated 20 hour plasma concentration (ng/mL) profiles of desglymidodrine for once daily 20 mg formulation of the present disclosure compared to TID immediate release 5 mg tablets.

The same modeling method used in Example 2 was used to simulate the plasma profiles of desglymidodrine after administration of the 20 mg FR+ER tablets compared to 5 mg immediate release tablets at 0, 4, and 8 hours (i.e., a TID regimen). The simulated desglymidodrine plasma profile for the 20 mg FR+ER tablet also achieved a higher initial desglymidodrine plasma level (greater than 14 ng/mL) within 1 hour compared to the simulated plasma profile for the 5 mg immediate release (TID). Furthermore, the 20 mg FR+ER tablet maintain desglymidodrine level of at least about 10 mg/mL over at least about 10 hours as shown FIG. 6.

These simulated plasma profiles show a faster level of desglymidodrine (greater than 14 ng/mL) achieved within about 1 hour compared to the first dose of 5 mg immediate release TID regimen. The simulated plasma profiles also show sustained levels of desglymidodrine (at least 10 ng/mL) over a period of about 10 hours.

Example 4

Midodrine HCl Fast Release Core Coated with an Extended Release Coating and an Fast Release Drug Coating A 45 mg fast release core coated with an extended release coating followed by a fast release drug coating can be prepared using the components shown in TABLE 2. Midodrine HCl is blended with microcrystalline cellulose and lubricated with colloidal silicone dioxide and magnesium stearate. This lubricated blend is compressed into a fast release core tablet. The tablets are coated with ethyl cellulose aqueous dispersion and hypromellose to form an extended release film. The coated extended release tablets are further coated with an aqueous solution of Midodrine HCl and hypromellose to form an outer fast release drug coat on the tablets.

TABLE 2

| Ingredient No. | Ingredient | mg/unit |
|---|---|---|
| | Fast Release Core | |
| 1 | Midodrine HCl | 31.50 |
| 2 | Microcrystalline Cellulose | 66.00 |
| 3 | Colloidal Silicon Dioxide | 1.50 |
| 4 | Magnesium Stearate | 1.00 |
| | Total | 100.00 |
| | Extended Release Coating | |
| 5 | Ethyl cellulose aqueous dispersion | 9.60 |
| 6 | Hypromellose | 6.40 |
| 7 | Purified Water | QS |
| 8 | Total | 16.00 |

TABLE 2-continued

| Ingredient No. | Ingredient | mg/unit |
|---|---|---|
| | Fast Release Drug Coating | |
| 9 | Midodrine HCl | 13.50 |
| 10 | Hypromellose | 10.50 |
| 11 | Purified water | QS |
| 12 | Total | 24.00 |
| | TOTAL | 140.00 |

Example 5

Midodrine HCl Capsule Filled with Pellets Having an Extended Release Core and Fast Release Coating A 30 mg capsule filled with pellets having an extended release core and fast release coating can be prepared using the components shown in TABLE 3. Midodrine HCl, microcrystalline cellulose and hypromellose are blended and granulated using aqueous solution of povidone in a high shear granulator. The wet mass is extruded and spheronized using extrusion and spheronizer to form wet spherical pellets. These extended release matrix pellets are dried in a fluid bed dryer and further coated with an aqueous solution of midodrine HCl and hypromellose to form an outer fast release drug layer. These pellets are filled in to a size 1 capsule using capsule filling machine.

TABLE 3

| Ingredient No. | Ingredient | mg/capsule |
|---|---|---|
| | Extended Release Core | |
| 1 | Midodrine HCl | 21.00 |
| 2 | Microcrystalline Cellulose | 128.00 |
| 3 | Hypromellose | 210.00 |
| 4 | Povidone | 11.00 |
| 5 | Purified water | QS |
| | Total | 370.00 |
| | Fast Release Drug Coating | |
| 6 | Midodrine HCl | 9.00 |
| 7 | Hypromellose | 11.00 |
| 8 | Purified water | QS |
| 9 | Total | 20.00 |
| | TOTAL | 390.00 |
| 10 | Size 1 capsule | 96.00 |
| | TOTAL | 486.00 |

Example 6

Midodrine HCl Bi-Layer Extended Release Tablet Having an Fast and an Extended Release Layer, Prepared by Direct Compression Method A 18 mg bi-layer extended release tablet with fast and extended release layers can be prepared using components shown in TABLE 4. For the fast release layer, Midodrine HCl, microcrystalline cellulose, sodium starch glycolate and iron oxide yellow are blended and lubricated using talc and magnesium stearate. For the extended release layer, Midodrine HCl, microcrystalline cellulose and hypromellose are blended and lubricated using colloidal silicon dioxide and magnesium stearate. These lubricated layers are then compressed into bi-layer tablets using a bi-layer tablet press.

TABLE 4

| No. | Ingredients | mg/tablet |
|---|---|---|
|  | Fast release layer |  |
| 1 | Midodrine HCl | 5.40 |
| 2 | Microcrystalline cellulose | 142.60 |
| 3 | Sodium starch glycolate | 9.60 |
| 4 | Iron oxide yellow | 0.80 |
| 5 | Talc | 0.80 |
| 6 | Magnesium stearate | 0.80 |
|  | Total | 160.00 |
|  | Extended release layer |  |
| 7 | Midodrine HCl | 12.60 |
| 8 | Microcrystalline cellulose | 178.20 |
| 9 | Hypromellose | 126.00 |
| 10 | Colloidal silicon dioxide | 1.60 |
| 11 | Magnesium stearate | 1.60 |
|  | Total | 320.00 |
|  | Final tablet weight | 480.00 |

Example 7

Figure 7:
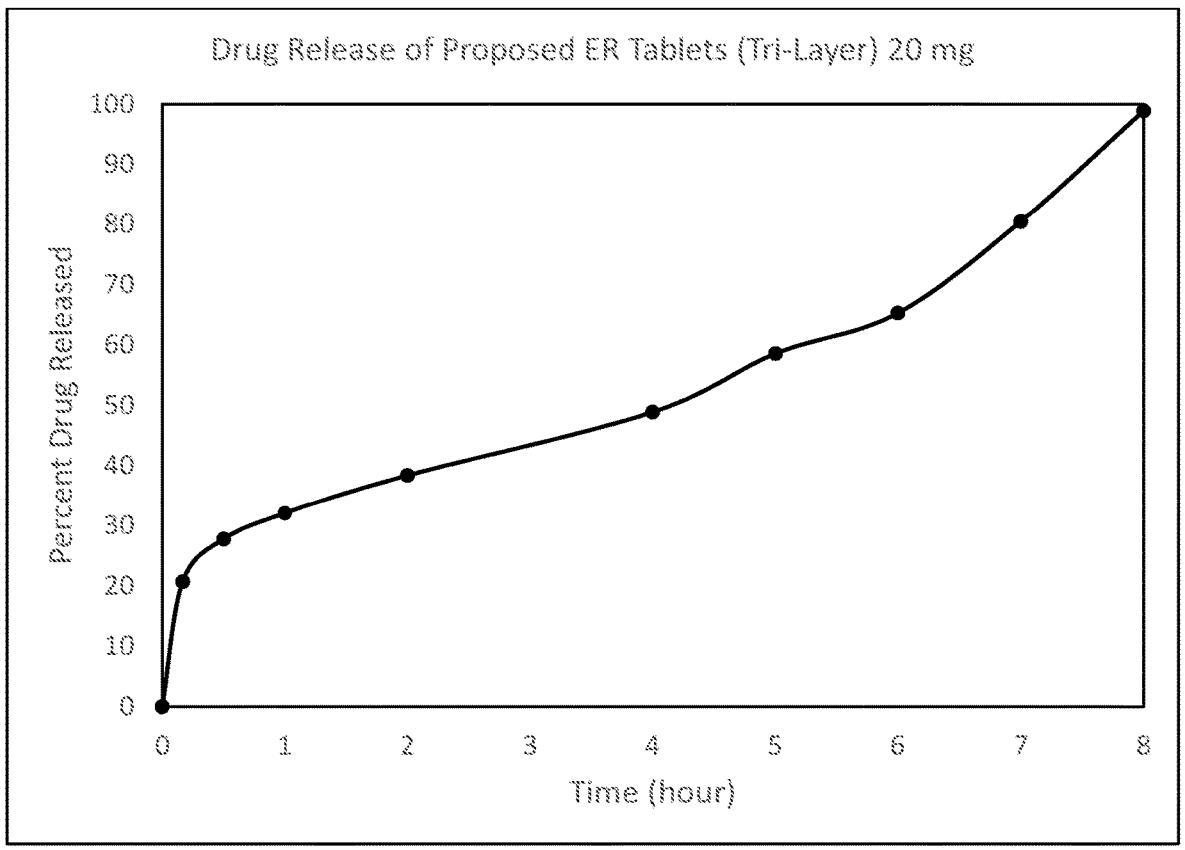
FIG. 7 shows simulated drug release profile (shown as %/hr) over time for a tri-layer tablet formulation containing 20 mg of midodrine HCl.
Figure 8:
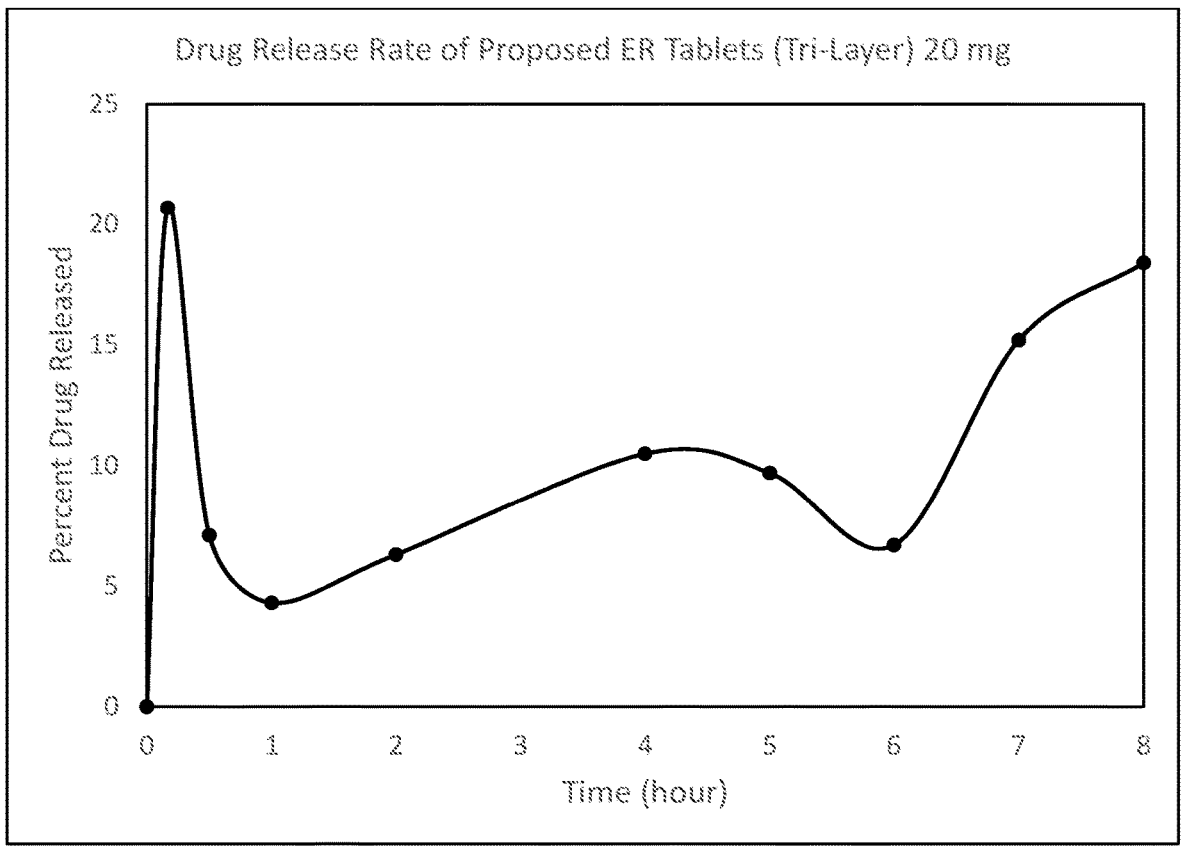
FIG. 8 is a graph that illustrates the drug release rate (shown as %/hr) over time for a fast release/extended release tri-layer tablet formulation containing 20 mg of midodrine HCl.

Midodrine HC Tri-Layer Extended Release Tablet Having an Fast and Two Extended Release Layers, Prepared by Direct Compression Method A 20 mg tri-layer extended release tablet with one fast layer and two extended release layers can be prepared using components shown in TABLE 5. For the fast release layer, Midodrine HCl, microcrystalline cellulose, crospovidone and iron oxide yellow are blended and lubricated using talc and magnesium stearate. For the first extended release layer, Midodrine HCl, microcrystalline cellulose, hypromellose and iron oxide red are blended and lubricated using colloidal silicon dioxide and magnesium stearate. For the second extended release layer, Midodrine HCl, microcrystalline cellulose and hypromellose are blended and lubricated using colloidal silicon dioxide and magnesium stearate. These lubricated layers are then compressed into tri-layer tablets using a multi-layer tablet press. Drug release profile and release rate (shown as %/hr) over time for the tri-layer tablet formulation are shown in FIGS. 7 and 8, respectively.

TABLE 5

| No. | Ingredients | mg/tablet |
|---|---|---|
|  | Fast release layer |  |
| 1 | Midodrine HCl | 5.00 |
| 2 | Microcrystalline cellulose | 143.00 |
| 3 | Crospovidone | 9.60 |
| 4 | Iron oxide yellow | 0.80 |
| 5 | Talc | 0.80 |
| 6 | Magnesium stearate | 0.80 |
|  | Total | 160.00 |
|  | 1$^{st}$ Extended release layer |  |
| 7 | Midodrine HCl | 10.00 |
| 8 | Microcrystalline cellulose | 99.60 |
| 9 | Hypromellose | 48.00 |
| 10 | Iron oxide red | 0.80 |
| 11 | Colloidal silicon dioxide | 0.80 |

TABLE 5-continued

| No. | Ingredients | mg/tablet |
|---|---|---|
| 12 | Magnesium stearate | 0.80 |
|  | Total | 160.00 |
|  | 2$^{nd}$ Extended release layer |  |
| 13 | Midodrine HCl | 5.00 |
| 14 | Microcrystalline cellulose | 133.40 |
| 15 | Eudragit ® L 30D 55 (30% w/w aqueous dispersion) | 20.00 |
| 16 | Colloidal silicon dioxide | 0.80 |
| 17 | Magnesium stearate | 0.80 |
|  | Total | 160.00 |
|  | Final tablet weight | 480.00 |

Example 8

Midodrine HCl Extended Release Hydrophilic Matrix Core, Prepared in a High Shear Granulator by Wet Granulation Method, Coated with an Fast Release Drug Coat by Perforated Pan Coating Method A 24 mg tablet with an extended release hydrophilic matrix core and a fast release drug coat over the extended release core can be prepared using components shown in TABLE 6. Midodrine HCl, microcrystalline cellulose and hydroxypropyl cellulose are blended in a high shear granulator. The blend is granulated by a wet granulation method using purified water. The granules are dried, milled and lubricated using colloidal silicon dioxide and magnesium stearate. The lubricated blend is compressed into extended release core tablets. These extended release core tablets are coated with a fast release drug coat solution containing Midodrine HCl, hypromellose, polyethylene glycol and purified water in a perforated coating pan.

TABLE 6

| No. | Ingredients | mg/tablet |
|---|---|---|
|  | Extended release core |  |
| 1 | Midodrine HCl | 18.00 |
| 2 | Microcrystalline cellulose | 121.50 |
| 3 | Hydroxypropyl cellulose | 108.00 |
| 4 | Purified water | QS |
| 5 | Colloidal silicon dioxide | 1.25 |
| 6 | Magnesium stearate | 1.25 |
|  | Total | 250.00 |
|  | Fast release drug coat |  |
| 7 | Midodrine HCl | 6.00 |
| 8 | Hypromellose | 12.80 |
| 9 | Polyethylene glycol | 1.20 |
| 10 | Purified water | QS |
|  | Total | 20.00 |
|  | Final tablet weight | 270.00 |

Example 9

Midodrine HCl Extended Release Hydrophilic Matrix Core, Prepared by Direct Compression Method, Coated with a Water-Permeable Functional Coat Followed by a Fast Release Drug Coat in a Perforated Coating Pan A 27 mg tablet with an extended release hydrophilic matrix core, a water-permeable functional coating, and a fast release drug coating is prepared using components shown in TABLE 7. Midodrine HCl, lactose monohydrate and hypromellose are blended and lubricated using talc and magnesium stearate. The lubricated blend is compressed into extended release core tablets. These tablets are coated with a functional coating containing an aqueous dispersion of Surelease® and Opadry® Clear. The tablets are further coated with a fast release drug coating containing Midodrine HCl, croscarmellose sodium, hydroxypropyl cellulose, polyethylene glycol, and purified water.

TABLE 7

| No. | Ingredients | mg/tablet |
| --- | --- | --- |
| | Extended release core | |
| 1 | Midodrine HCl | 21.00 |
| 2 | Lactose monohydrate | 33.00 |
| 3 | Hypromellose | 144.00 |
| 4 | Talc | 1.00 |
| 5 | Magnesium stearate | 1.00 |
| | Total | 200.00 |
| | Functional coat | |
| 6 | Surelease ® (30% w/w aqueous dispersion) | 9.00 |
| 7 | Opadry ® Clear | 6.00 |
| 8 | Purified water | QS |
| | Total | 15.00 |
| | Sub total | 215.00 |
| | Fast release drug coat | |
| 9 | Midodrine HCl | 6.00 |
| 10 | Croscarmellose Sodium | 4.00 |
| 11 | Hydroxypropyl cellulose | 13.60 |
| 12 | Polyethylene glycol | 1.40 |
| 13 | Purified water | QS |
| | Total | 25.00 |
| | Final tablet weight | 240.00 |

Example 10

Midodrine HCl Tablet-in-Tablet with an Extended Release Core, Prepared by Top Spray Granulation Method, Covered with a Fast Release Drug Coat by Tablet-in-Tablet Compression Method A 15 mg tablet-in-tablet with an extended release tablet in a fast release tablet can be prepared using components shown in TABLE 8. For extended release core tablet, Midodrine HCl and Lactose monohydrate are blended and granulated using Surelease® by top spray granulation in a fluid bed processor. The granules are dried, milled and lubricated using talc and magnesium stearate. For the fast release outer tablet, a blend of Midodrine HCl, crospovidone and iron oxide red is geometrically mixed with microcrystalline cellulose. The blend is then lubricated with talc and magnesium stearate. Using a specially designed tablet-in-tablet compression machine, the extended release core tablet is compressed followed by compression of the outer fast release tablet around the extended release core tablet.

TABLE 8

| No. | Ingredients | mg/tablet |
| --- | --- | --- |
| | Extended release core | |
| 1 | Midodrine HCl | 12.00 |
| 2 | Lactose monohydrate | 57.00 |
| 3 | Surelease ® (30% w/w aqueous dispersion) | 30.00 |
| 4 | Talc | 0.50 |
| 5 | Magnesium stearate | 0.50 |
| | Total | 100.00 |
| | Fast release outer coat | |
| 6 | Midodrine HCl | 3.00 |
| 7 | Microcrystalline cellulose | 182.80 |
| 8 | Crospovidone | 12.00 |
| 9 | Iron oxide red | 0.20 |
| 10 | Talc | 1.00 |
| 11 | Magnesium stearate | 1.00 |
| | Total | 200.00 |
| | Final tablet weight | 300.00 |

Example 11

Midodrine HCl Extended Release Hydrophobic Core, Prepared by Melt Granulation Method, Coated with a Fast Release Drug Coat by Compression Coating Method A 45 mg compression coated tablet having an extended release hydrophobic core and a fast release outer coating can be prepared using components shown in TABLE 9. For the extended release core tablet, Midodrine HCl, microcrystalline cellulose and hydrogenated castor oil are blended in steam jacketed high shear mixer granulator. The blend is then granulated by melting hydrogenated castor oil with the help of steam. The granules are cooled, milled, and lubricated using sodium stearyl fumarate. For the fast release outer coat tablet, a blend of Midodrine HCl, sodium starch glycolate and iron oxide red is geometrically mixed with microcrystalline cellulose. The blend is then lubricated with talc and magnesium stearate. Using a specially designed compression machine, the extended release core tablet is compressed followed by compression of the outer fast release coat tablet.

TABLE 9

| No. | Ingredients | mg/tablet |
| --- | --- | --- |
| | Extended release core | |
| 1 | Midodrine HCl | 30.00 |
| 2 | Microcrystalline cellulose | 16.00 |
| 3 | Hydrogenated castor oil | 150.00 |
| 4 | Sodium stearyl fumarate | 4.00 |
| | Total | 200.00 |
| | Fast release outer coat | |
| 5 | Midodrine HCl | 15.00 |
| 6 | Microcrystalline cellulose | 167.80 |
| 7 | Sodium starch glycolate | 15.00 |

TABLE 9-continued

| No. | Ingredients | mg/tablet |
|---|---|---|
| 8 | Iron oxide red | 0.20 |
| 9 | Talc | 1.00 |
| 10 | Magnesium stearate | 1.00 |
|  | Total | 200.00 |
|  | Final tablet weight | 400.00 |

Example 12

Midodrine HCl Extended Release Capsule Containing Fast and Extended Release Pellets, Prepared by Drug Layering and Functional Coating Method A 15 mg extended release capsule containing a fast release pellets and functional coated extended release pellets can be prepared using components shown in TABLE 10. A drug layering dispersion containing Midodrine HCl, hypromellose, and talc in purified water is layered on to microcrystalline cellulose spheres in fluid bed processor by bottom spray method to prepare fast release pellets. A portion of these drug-layered pellets is coated with an ethanolic solution of ethylcellulose and oleic acid to form extended release pellets. Then the fast release and extended release pellets are lubricated with talc and magnesium stearate and filled into capsules.

TABLE 10

| No. | Ingredient | mg/capsule |
|---|---|---|
| | Fast release pellets | |
| 1 | Microcrystalline cellulose spheres | 74.00 |
| 2 | Midodrine HCl | 15.00 |
| 3 | Hypromellose | 10.00 |
| 4 | Talc | 1.00 |
| 5 | Purified water | QS |
| | Total | 100.00 |
| | Extended release pellets | |
| 6 | Fast release pellets | 60.00 |
| 7 | Ethylcellulose | 10.00 |
| 8 | Oleic acid | 2.00 |
| 9 | Ethanol | QS |
| | Total | 72.00 |
| | Capsule filling | |
| 10 | Fast release pellets | 40.00 |
| 11 | Extended release pellets | 72.00 |
| 12 | Talc | 1.50 |
| 13 | Magnesium stearate | 0.50 |
| 14 | Size 2 capsule | 60.00 |
| | Filled capsule weight | 174.00 |

Example 13

Midodrine Extended Release Capsule Containing Fast and Extended Release Pellets, Prepared by Drug Layering and Functional Coating Method A 20 mg extended release capsule containing fast release pellets and functional coated extended release pellets can be prepared using components shown in TABLE 11. A drug layering dispersion containing Midodrine HCl, hypromellose and talc in purified water is layered on to microcrystalline cellulose spheres in fluid bed processor by bottom spray method to prepare fast release pellets. One portion (50%) of these drug-layered pellets is coated with an ethanolic solution of ethylcellulose and oleic acid to form a first population of extended release pellets. A second portion (20%) of the drug-layered pellets is coated with an aqueous dispersion of Eudragit® L 30D 55 to form a second population of extended release pellets. Then the fast release and extended release pellets are lubricated with talc and magnesium stearate and filled in to capsules.

TABLE 11

| No. | Ingredient | mg/capsule |
|---|---|---|
| | Fast release pellets | |
| 1 | Microcrystalline cellulose spheres | 69.00 |
| 2 | Midodrine HCl | 20.00 |
| 3 | Hypromellose | 10.00 |
| 4 | Talc | 1.00 |
| 5 | Purified water | QS |
| | Total | 100.00 |
| | $1^{st}$ Extended release pellets | |
| 6 | Fast release pellets | 50.00 |
| 7 | Ethylcellulose | 9.00 |
| 8 | Oleic acid | 1.00 |
| 9 | Ethanol | QS |
| | Total | 60.00 |
| | $2^{nd}$ Extended release pellets | |
| 10 | Fast release pellets | 20.00 |
| 11 | Eudragit ® L 30D 55 (30% w/w aqueous dispersion) | 20.00 |
| 12 | Purified water | QS |
| | Total | 40.00 |
| | Capsule filling | |
| 13 | Fast release pellets | 30.00 |
| 14 | $1^{st}$ Extended release pellets | 60.00 |
| 15 | $2^{nd}$ Extended release pellets | 40.00 |
| 16 | Talc | 1.50 |
| 17 | Magnesium stearate | 0.50 |
| 18 | Size 1 capsule | 76.00 |
| | Filled capsule weight | 208.00 |

Example 14

Midodrine HCl Orally Disintegrating Extended Release Tablet Containing Fast and Extended Release Pellets A 15 mg orally disintegrating extended release tablet containing fast release and functional coated extended release pellets can be prepared using components shown in TABLE 12. A drug layering dispersion containing Midodrine HCl, hypromellose and talc in purified water is layered on to microcrystalline cellulose spheres in fluid bed processor by bottom spray method to prepare drug-layered pellets. These pellets are then coated with an ethanolic solution of ethylcellulose and oleic acid to form extended release pellets. These extended release pellets are further coated with a fast release drug coating using aqueous dispersion containing Midodrine HCl, hypromellose and talc. The pellets are then blended with microcrystalline cellulose, mannitol, croscarmellose sodium, aspartame and peppermint flavor and lubricated Magnesium stearate. The lubricated blend is then compressed into orally disintegrating tablets.

TABLE 12

| No. | Ingredients | mg/tablet |
|---|---|---|
| | Drug layered pellets | |
| 1 | Microcrystalline cellulose spheres | 44.50 |
| 2 | Midodrine HCl | 9.00 |
| 3 | Hypromellose | 6.00 |
| 4 | Talc | 0.50 |
| 5 | Purified water | QS |
| | Total | 60.00 |
| | Functional coating | |
| 6 | Ethylcellulose | 10.00 |
| 7 | Oleic acid | 2.00 |
| 8 | Ethanol | QS |
| | Total | 12.00 |
| | Sub total | 72.00 |
| | Fast release drug coat | |
| 9 | Functional coated extended release pellets | 72.00 |
| 10 | Midodrine HCl | 6.00 |
| 11 | Hypromellose | 4.00 |
| 12 | Talc | 1.00 |
| 13 | Purified water | QS |
| | Total | 83.00 |
| | Tableting | |
| 14 | Fast release drug coated extended release pellets | 83.00 |
| 15 | Microcrystalline cellulose | 161.00 |
| 16 | Mannitol | 108.00 |
| 17 | Croscarmellose sodium | 24.00 |
| 18 | Aspartame | 12.00 |
| 19 | Peppermint flavor | 8.00 |
| 20 | Magnesium stearate | 4.00 |
| | Final tablet weight | 400.00 |

Example 15

Midodrine HCl Extended Release Sachet for Reconstitution Containing Extended Release Pellets Coated with a Fast Release Drug Coat A 30 mg extended release sachets containing extended release pellets coated with a fast release drug coat can be prepared using components shown in TABLE 13. Midodrine HCl, microcrystalline cellulose and hypromellose are mixed and granulated with a non-aqueous solution of povidone in a high shear granulator. The wet mass is extruded and the extrudes are spheronized to form spherical pellets. These extended release pellets are then dried, sized, and coated with a seal coating solution in fluid bed processor by bottom spray method. The seal coated pellets are further coated with a fast release drug coating. These pellets are then blended with xanthan gum, mannitol, orange flavor and lubricated with magnesium stearate. The blend is then filled in to sachets. The content of sachet is reconstituted with water at the time of administration to form an extended release suspension.

TABLE 13

| No. | Ingredients | mg/sachet |
|---|---|---|
| | Extended release pellets | |
| 1 | Midodrine HCl | 21.00 |
| 2 | Microcrystalline cellulose | 90.00 |
| 3 | Hypromellose | 168.00 |
| 4 | Povidone | 21.00 |
| 5 | Isopropyl alcohol | QS |
| | Total | 300.00 |
| | Seal coating | |
| 6 | Opadry ® Clear | 30.00 |
| 7 | Purified water | QS |
| | Total | 30.00 |
| | Sub total | 330.00 |
| | Fast release drug coat | |
| 8 | Midodrine HCl | 9.00 |
| 9 | Hypromellose | 19.00 |
| 10 | Talc | 2.00 |
| 11 | Purified water | QS |
| | Total | 30.00 |
| | Sub total | 360.00 |
| | Sachet filling | |
| 14 | Extended release pellets | 360.00 |
| 15 | Xanthan gum | 18.00 |
| 16 | Mannitol | 207.00 |
| 17 | Orange flavor | 12.00 |
| 18 | Magnesium stearate | 3.00 |
| | Sachet filled weight | 600.00 |

Example 16

Midodrine HCl Extended Release Tablets Based on Osmotic Drug Delivery, Prepared by Top Spray Granulation Method Coated with a Fast Release Drug Coat in a Perforated Coating Pan A 60 mg extended release tablets based on osmotic drug delivery can be prepared using components shown in TABLE 14. For the extended release drug layer, Modidrine HCl, microcrystalline cellulose, polyethylene oxide are granulated in a fluid bed processor using purified water by top spray granulation. The granules are dried, milled, and lubricated using magnesium stearate. The push layer is also prepared by top spray granulation similar to the extended release drug layer. Both the layers are then compressed into bi-layer tablets using a multi-layer tablet compression machine. These tablets are then coated with a functional coating solution of cellulose acetate and polyethylene glycol in acetone and purified water mixture. These tablets are then passed through a laser drilling machine to drill an orifice in the drug layer side. The tablets are then coated with an aqueous solution of Midodrine HCl and hypromellose to form a fast release drug coat.

TABLE 14

| No. | Ingredients | mg/tablet |
|---|---|---|
| | Drug layer | |
| 1 | Midodrine HCl | 42.00 |
| 2 | Microcrystalline cellulose | 108.40 |

TABLE 14-continued

| No. | Ingredients | mg/tablet |
|---|---|---|
| 3 | Polyethylene oxide | 168.00 |
| 4 | Purified water | QS |
| 5 | Magnesium stearate | 1.60 |
| | Total | 320.00 |
| | Push layer | |
| 6 | Polyethylene oxide | 219.20 |
| 7 | Sodium chloride | 80.00 |
| 8 | Povidone | 16.00 |
| 9 | Iron oxide red | 3.20 |
| 10 | Purified water | QS |
| 11 | Magnesium stearate | 1.60 |
| | Total | 320.00 |
| | Sub total | 640.00 |
| | Functional coating | |
| 12 | Cellulose acetate | 80.00 |
| 13 | Polyethylene glycol | 16.00 |
| 14 | Acetone | QS |
| 15 | Purified water | QS |
| | Total | 96.00 |
| | Sub total | 736.00 |
| | Fast release drug coat | |
| 16 | Midodrine HCl | 18.00 |
| 17 | Hypromellose | 26.00 |
| 18 | Purified water | QS |
| | Total | 44.00 |
| | Final tablet weight | 780.00 |

Example 17

Midodrine HCl Bi-Layer Extended Release Tablet Having a Fast Release and an Extended Release Layer, Prepared by Slugging Method A 20 mg bi-layer extended release tablet with fast and extended release layers can be prepared by a slugging method using components shown in TABLE 15. For the fast release layer, midodrine HCl, silicified microcrystalline cellulose, croscarmellose sodium and iron oxide red are blended and lubricated using talc and magnesium stearate. For extended release layer, midodrine HCl, methacrylic acid and ethyl acrylate copolymer (1:1), and povidone are blended and lubricated using glyceryl behenate and are converted into slugs. The slugs are milled to desired granule size and lubricated using magnesium stearate. The lubricated layers are then compressed into bi-layer tablets.

TABLE 15

| No. | Ingredients | mg/tablet |
|---|---|---|
| | Fast release layer | |
| 1 | Midodrine HCl | 4.00 |
| 2 | Microcrystalline cellulose | 134.75 |
| 3 | Croscarmellose sodium | 9.00 |
| 4 | Iron oxide red | 0.75 |
| 5 | Talc | 0.75 |
| 6 | Magnesium stearate | 0.75 |
| | Total | 150.00 |
| | Extended release layer | |
| 7 | Midodrine HCl | 16.00 |
| 8 | Methacrylic acid and ethyl acrylate copolymer (1:1) | 262.50 |
| 9 | Povidone | 20.00 |
| 10 | Glyceryl behenate | 20.00 |
| 11 | Magnesium stearate | 1.50 |
| | Total | 320.00 |
| | Final tablet weight | 470.00 |

Figure 9:
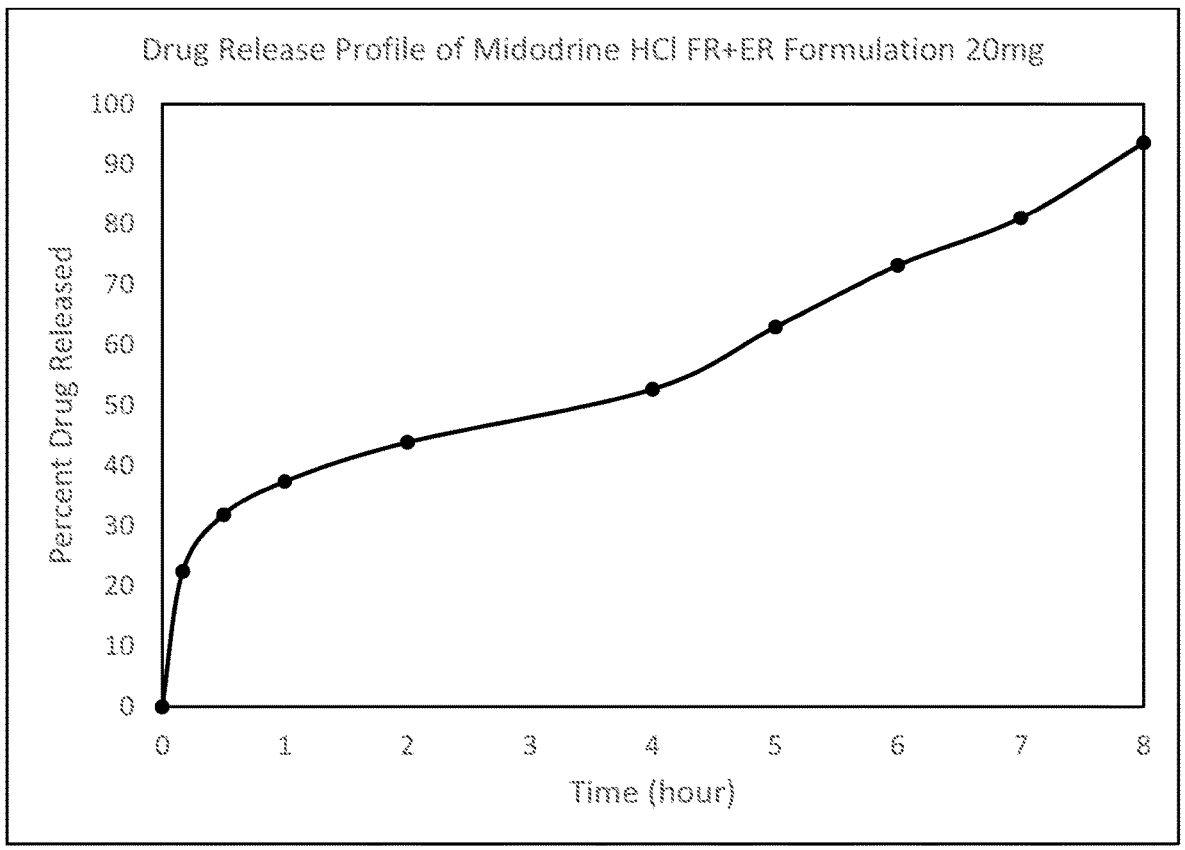
FIG. 9 shows dissolution profile for the midodrine HCl 20 mg formulation of Example 17.

FIG. 9 shows dissolution profile for midodrine HCl 20 mg tablet discussed above, using USP apparatus 1 (Basket) at 100 RPM in 900 mL pH 1.2 (0.1N Hydrochloric acid) 0-2 hr; pH 4.5 (Acetate buffer) 2-4 hr; pH 6.8 (Phosphate buffer) 4 hr onwards.

What is claimed is:

1. A pharmaceutical composition comprising:
   a first release portion comprising an active agent in a range of about 20% to about 40% (w/w) of a total amount of the active agent in the composition;
   a second release portion comprising the active agent in a range of about 60% to about 80% (w/w) of the total amount of the active agent in the composition; and
   a rate controlling agent, wherein the rate controlling agent is selected from the group consisting of a water-soluble excipient, a water-insoluble excipient, a water permeable excipient, and a combination thereof, and wherein the rate controlling agent is present in a weight ratio of the active agent in the second release portion of the composition to the rate controlling agent of about 1:1 to about 1:30 (w/w);
   wherein the in vitro release rate of the active agent, measured by an in vitro dissolution test comprises (i) a first release that is relatively fast and (ii) a second release, wherein the second release does not include a second rise in release rate that takes place about 5 hours to about 10 hours after start of the in vitro dissolution test,
   wherein the active agent is selected from the group consisting of midodrine, a pharmaceutically acceptable salt of midodrine, desglymidodrine, a pharmaceutically acceptable salt of desglymidodrine, and any combination thereof; and
   wherein the second release comprises a second rise in release rate that takes place about 2 to about 4.5 hours after start of the in vitro dissolution test.

2. The pharmaceutical composition of claim 1, further comprising:
   (iii) a third release which includes a third rise in release rate that takes place about 5 hours to about 8 hours after start of the in vitro dissolution test, and
   wherein the active agent is selected from the group consisting of midodrine, a pharmaceutically acceptable salt of midodrine, desglymidodrine, a pharmaceutically acceptable salt of desglymidodrine, and any combination thereof.

3. The pharmaceutical composition of claim 1, wherein the first release portion comprises about 1.5 mg to about 45 mg of active agent and an excipient, wherein the active agent is present in an amount of about 2% to about 40% of the total weight of the first release portion; and the second release portion comprises about 3.5 mg to about 105 mg of active agent and a rate controlling agent, wherein the active agent is present in an amount of about 2% to about 20% of the total weight of the second release portion, and the amount of active agent in the second release portion to the amount of rate controlling agent is a ratio of about 1:1 to about 1:30 (w/w), and the total amount of the active agent is about 5 mg to about 150 mg.

4. The pharmaceutical composition of claim 1, wherein substantially all of the active agent in the first release portion is released within about 1 hour after administration of the pharmaceutical composition to a subject; and substantially all of the active agent in the second release portion is released over a period of time between about 1 hour after administration of the composition to the subject and up to about 16 hours after administration of the composition to a subject.

5. The pharmaceutical composition of claim 1, wherein the in vitro dissolution test was performed with USP Apparatus I (baskets) at 100 rpm in 900 mL at 37° C. for 0-2 hours in 0.1N HCl (pH 1.2); for 2-4 hours in acetate buffer (pH 4.5); and for 4-16 hours or 4-12 hours in phosphate buffer (pH 6.8).

6. The pharmaceutical composition of claim 1, wherein at least about 20% of the total amount of active agent in the composition is released within about 1 hour and at least about 80% of the total amount of active agent in the composition is released within about 12 hours after the start of an in vitro dissolution test.

7. The pharmaceutical composition of claim 1, wherein the active agent is present in a total amount of about 7.5 mg to about 120 mg.

8. The pharmaceutical composition of claim 1, wherein the in vitro release rate of the active agent during the second release phase is slower compared to the in vitro release rate of the active agent released during the first release phase.

9. The pharmaceutical composition of claim 1, wherein the rate controlling agent is present in a weight ratio of the active agent in the second release portion of the composition to the rate controlling agent of about 1:5 to about 1:15 (w/w).

10. The pharmaceutical composition of claim 1, wherein the pharmaceutical composition is a multilayer tablet, or a capsule comprising a plurality of fast release pellets and a plurality of extended release pellets.

11. The pharmaceutical composition of claim 1, wherein the active agent is present in the first release portion in an amount of about 1.5 mg to about 45 mg, and in the second release portion in an amount of about 3.5 mg to about 105 mg.

12. The pharmaceutical composition of claim 1, wherein administration of the pharmaceutical composition to a subject provides (i) a relatively fast peak plasma concentration reaching at least about 12 ng/ml of desglymidodrine within about 1 hour and (ii) a plasma concentration of desglymidodrine of at least about 7 ng/ml or at least about 10 ng/ml for at least about 8 hours or at least about 10 hours.

13. The pharmaceutical composition of claim 1, wherein the pharmaceutical composition is a multi-layer tablet, a capsule, or suspension, wherein:

the first release portion comprises an amount of the active agent in the range of about 1.5 mg to 45 mg; the second release portion comprises an amount of the active agent in the range of about 3.5 mg to about 105 mg; and the first release portion releases at least about 20% to about 40% w/w of the total amount of the active agent in the tablet, capsule, or suspension within about 1 hour and the second release portion releases the remaining total amount of the active agent in the tablet, capsule, or suspension at a slower rate than the release rate of the first release portion in an in vitro dissolution test.

14. The pharmaceutical composition of claim 13, wherein the second release portion comprises a rate controlling agent, wherein the rate controlling agent is selected from the group consisting of a water soluble excipient, a water-insoluble excipient, a water permeable excipient, and a combination thereof, and wherein the amount of active agent in the second release portion to the amount of rate controlling agent is a ratio of about 1:1 to about 1:30 (w/w), optionally about 1:5 to about 1:15 (w/w).

15. The pharmaceutical composition of claim 13, wherein the second release portion further comprises a-rate controlling agent comprises comprising a methacrylic acid copolymer and a fatty acid ester.

16. A method for treating orthostatic hypotension or postural orthostatic tachycardia syndrome (POTS) in a subject comprising administering the pharmaceutical composition of claim 1 to a subject in need thereof.

17. The method of claim 16, wherein a single dose of the pharmaceutical composition comprises about 10% to 70% more than the total amount of active agent in three 2.5 mg, 5 mg, or 10 mg immediate release tablets.

18. A kit comprising:

a first formulation and a second formulation, wherein the first and second formulations comprise the same active agent or different active agents, and the first formulation comprises a pharmaceutical composition of claim 1.

* * * * *